US012059529B2

(12) United States Patent
Tebbutt et al.

(10) Patent No.: US 12,059,529 B2
(45) Date of Patent: Aug. 13, 2024

(54) HEADGEAR ASSEMBLY WITH SEMI-RIGID SIDE ARMS

(71) Applicant: Fisher & Paykel Healthcare Limited, Auckland (NZ)

(72) Inventors: Adam Alexander Tebbutt, Auckland (NZ); Matthew Roger Stephenson, Auckland (NZ); Bruce Michael Walls, Auckland (NZ); Priyanka Ferdinand Pereira, Auckland (NZ); Paul Mathew Freestone, Auckland (NZ); Melissa Catherine Bornholdt, Auckland (NZ); Jake Baker Hocking, Auckland (NZ); Abby Rebecca Farrow, Auckland (NZ); Chris Onin Limpin Hipolito, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 799 days.

(21) Appl. No.: 16/768,302

(22) PCT Filed: Dec. 4, 2018

(86) PCT No.: PCT/IB2018/059589
§ 371 (c)(1),
(2) Date: May 29, 2020

(87) PCT Pub. No.: WO2019/111135
PCT Pub. Date: Jun. 13, 2019

(65) Prior Publication Data

US 2021/0187234 A1 Jun. 24, 2021

Related U.S. Application Data

(60) Provisional application No. 62/594,927, filed on Dec. 5, 2017.

(51) Int. Cl.
*A61M 16/06* (2006.01)

(52) U.S. Cl.
CPC .............. *A61M 16/0694* (2014.02)

(58) Field of Classification Search
CPC .......... A61M 16/06–0694; A61M 2016/0661; A62B 18/02; A62B 18/025; A62B 23/02; A62B 23/025
See application file for complete search history.

(56) References Cited

U.S. PATENT DOCUMENTS

2006/0196511 A1* 9/2006 Lau .................. A61M 16/0666
128/207.18
2006/0218702 A1* 10/2006 Santos .................. A61B 90/50
2/422

(Continued)

OTHER PUBLICATIONS

International Search Report, PCT/IB2018/059589, dated Mar. 29, 2019, 8 pages.

*Primary Examiner* — Valerie L Woodward
(74) *Attorney, Agent, or Firm* — Knobbe, Martens, Olson & Bear, LLP

(57) ABSTRACT

A headgear assembly can include a pair of opposing, semi-rigid side arms. Each side arm can be pivotally coupled to an interface at a single location. Each side arm can extend from the single location across the user's cheeks and above the user's ears in use. The headgear assembly can include a top strap coupled to the pair of opposing, semi-rigid side arms, the top strap configured to extend around the top of a user's head. The headgear assembly can include a rear strap coupled to the pair of opposing, semi-rigid side arms, the rear strap configured to extend around the rear of a user's head. The headgear assembly can include a chin strap coupled to the pair of opposing, semi-rigid side arms, the chin strap configured to extend around the user's chin.

18 Claims, 22 Drawing Sheets

(56) References Cited

U.S. PATENT DOCUMENTS

| | | | |
|---|---|---|---|
| 2008/0190432 A1* | 8/2008 | Blochlinger | A61M 16/0616 128/207.18 |
| 2010/0229868 A1* | 9/2010 | Rummery | A61M 16/0666 264/156 |
| 2011/0220113 A1 | 9/2011 | Newman et al. | |
| 2011/0308520 A1 | 12/2011 | Mcauley et al. | |
| 2016/0067441 A1* | 3/2016 | Bearne | A61M 16/0605 128/205.25 |
| 2016/0287830 A1* | 10/2016 | Walls | A61M 16/0683 |
| 2017/0119988 A1 | 5/2017 | Allan et al. | |
| 2017/0326319 A1 | 11/2017 | Stephenson et al. | |

* cited by examiner

HEADGEAR ASSEMBLY WITH SEMI-RIGID SIDE ARMS

BACKGROUND

Field

The present disclosure relates to headgear assemblies for use in respiratory therapy. More particularly, certain aspects of the present disclosure relate to headgear assemblies including rigid side arms which are connected to the interface.

Description of Related Art

The treatment of respiratory ailments or conditions with therapies, such as NIV, Bi-level or CPAP, involves the delivery of pressurized air to the airways of a human via a conduit and a breathing apparatus (e.g., a mask or cannula). Typically, a mask creates at least a substantial "seal" on or around the nose and/or the mouth of a user while a cannula does not provide a seal but provides a delivery pathway for supplemental respiratory gas delivery.

A result of creating this "seal" is that the combination of the enclosure area of the breathing apparatus and its internal pressure creates a resulting force that attempts to push the breathing apparatus off of the face. To counteract this force, it is normal to use a headgear comprising a series of straps that pass around the back and/or top of a user's head. Headgear such as this are typically made from a compliant material, such as Breath-o-Prene™. The use of such a material results in the headgear having relatively little structure when not being worn. This lack of structure can give rise to the straps of the headgear becoming tangled, which in turn can make it difficult for a user to don the headgear and breathing apparatus.

The strap(s) require some form of adjustment to account for variation in head size, this adjustment mechanism is typically provided via an adjustment loop between the mask body and the head gear. The adjustment loop can have a hook-and-loop or similar fastener that permits an end of the strap to be passed through a mounting location on the mask or through a clip that attaches to the mask and then attached to another section of the strap. Such an arrangement permits adjustment of the headgear by positioning the end of the strap at a desired location on the other section of the strap to vary a size of the adjustment loop.

These types of mechanisms are one solution to providing an adjustment mechanism for the headgear and, thus, the interface assembly. Such systems also require a reasonable level of user interaction and, as a result, is prone to misuse or mis-adjustment (e.g., over-tightening). As a practical matter, micro-adjustment of such systems is difficult and time-consuming to accomplish. The creation of practical and not so practical solutions to this has been the subject of considerable development effort from a number of organizations, which has resulted in numerous patents.

Further, these traditional headgear are usually configured to have some elasticity. This can result in the headgear stretching over, and applying pinching forces to, the user's head, which can be uncomfortable. It is desirable to make headgear and breathing apparatus that are easy to use and comfortable to wear because this may improve a user's compliance with the therapy being provided.

SUMMARY

The systems and devices described herein have innovative aspects, no single one of which is indispensable or solely responsible for their desirable attributes. Without limiting the scope of the claims, some of the advantageous features will now be summarized.

In some embodiments, a headgear assembly is provided. The headgear assembly includes a pair of opposing, semi-rigid side arms, each side arm configured to be pivotally coupled to an interface at a single location, each side arm configured to extend from the single location across the user's cheeks and above the user's ears in use. The headgear assembly includes a top strap coupled to the pair of opposing, semi-rigid side arms, the top strap configured to extend over the top of a user's head. The headgear assembly includes a rear strap coupled to the pair of opposing, semi-rigid side arms, the rear strap configured to extend around the rear of a user's head. The headgear assembly includes a chin strap coupled to the pair of opposing, semi-rigid side arms, the chin strap configured to extend below the user's chin.

The headgear assembly includes an adjustment mechanism configured to allow movement between a semi-rigid side arm and the interface. In some embodiments, the adjustment mechanism includes a pair of components that are telescopically engaged. The headgear assembly includes the interface. In some embodiments, an upper portion of the pair of opposing, semi-rigid side arms is bifurcated. In some embodiments, the upper portion includes a top strap connection point configured to couple to the top strap. In some embodiments, the upper portion includes a rear strap connection point configured to couple to the rear strap. In some embodiments, a lower portion of the pair of opposing, semi-rigid side arms is bifurcated. In some embodiments, the lower portion includes a chin strap connection point configured to couple to the chin strap. In some embodiments, an upper portion of the pair of opposing, semi-rigid side arms is bifurcated and a lower portion of the pair of opposing, semi-rigid side arms is bifurcated. The headgear assembly includes a connecting member extending between the interface and a semi-rigid side arm. In some embodiments, the top strap and rear strap are arranged to form a bifurcated upper end of the headgear assembly and the chin strap and the connecting member form a bifurcated lower end of the headgear assembly. In some embodiments, the connecting member includes a twist such that the connecting member extends between an angled plane and a vertical plane. In some embodiments, the connecting member includes a male component of an adjustment mechanism. In some embodiments, the connecting member includes a bend. In some embodiments, the pair of opposing, semi-rigid side arms comprises an upper portion extending from an interface to a location above the user's ear and a lower portion having a first end that connects to the upper portion and a second end that connects to the interface below the connection of the upper portion. In some embodiments, the chin strap is configured to be a chin strap or a rear neck strap.

In some embodiments, a headgear assembly is provided. The headgear assembly includes a pair of side arms. Each side arm includes a translational adjustment mechanism configured to allow translational adjustment of the side arm. Each side arm includes a rotating adjustment mechanism configured to allow rotational adjustment of the side arm relative to an interface. In some embodiments, the rotating adjustment mechanism is vertically above the translational adjustment mechanism in use. In some embodiments, the rotating adjustment mechanism and the translational adjustment mechanism comprise a bend.

In some embodiments, a headgear assembly is provided. The headgear assembly includes a pair of side arms. Each side arm includes a first rotational adjustment mechanism configured to allow rotational adjustment of the side arm relative to an interface. Each side arm includes a second rotational adjustment mechanism configured to allow rotational adjustment between a lower member and an upper member of the side arm, wherein the first and second rotational adjustment mechanisms are spaced apart along the side arm.

In some embodiments, a headgear assembly is provided. The headgear assembly includes a pair of side arms. The headgear assembly includes a top strap, a rear strap, a first chin strap, and a second chin strap. In some embodiments, the first and second chin straps are spaced apart from each other and extend between the pair of side arms in use.

In some embodiments, a semi-rigid side arm for a side portion of a headgear assembly of a patient interface is provided. The semi-rigid side arm includes an elongate body extending between a first end and a second end. The semi-rigid side arm includes a first projection and a second projection projecting from the body at the first end. The semi-rigid side arm includes a third projection and a fourth projection projecting from the body at the second end. In some embodiments, each of the projections having a connection portion for connecting to straps of the headgear assembly or to the patient interface. In some embodiments, the elongate body and each of the projections have a thickness between 0.5 mm and 3 mm. In some embodiments, the elongate body extends along a longitudinal axis and wherein, the first and second projections project from the elongate body at different angles to each other and the third and fourth projections project from the elongate body at different angles to each other. In some embodiments, the first and third projections project away from the elongate body in substantially opposed directions, and the second and fourth projections project away from the elongate body in substantially opposed directions.

In some embodiments, an interface assembly for use in respiratory therapy is provided. The interface assembly includes an interface and a headgear assembly. In some embodiments, each side of the headgear assembly includes an upper portion connected to the interface and adapted to extend from the interface to a location above a user's ear. In some embodiments, each side of the headgear assembly includes a lower portion having a first end that connects to the upper portion and a second end that connects to the interface below the connection of the upper portion to the interface. In some embodiments, the connection location of at least one of the ends of the lower portion is adjustable. In some embodiments, the connection location of at least one of the ends of the lower portion is discretely adjustable.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Figure 1:
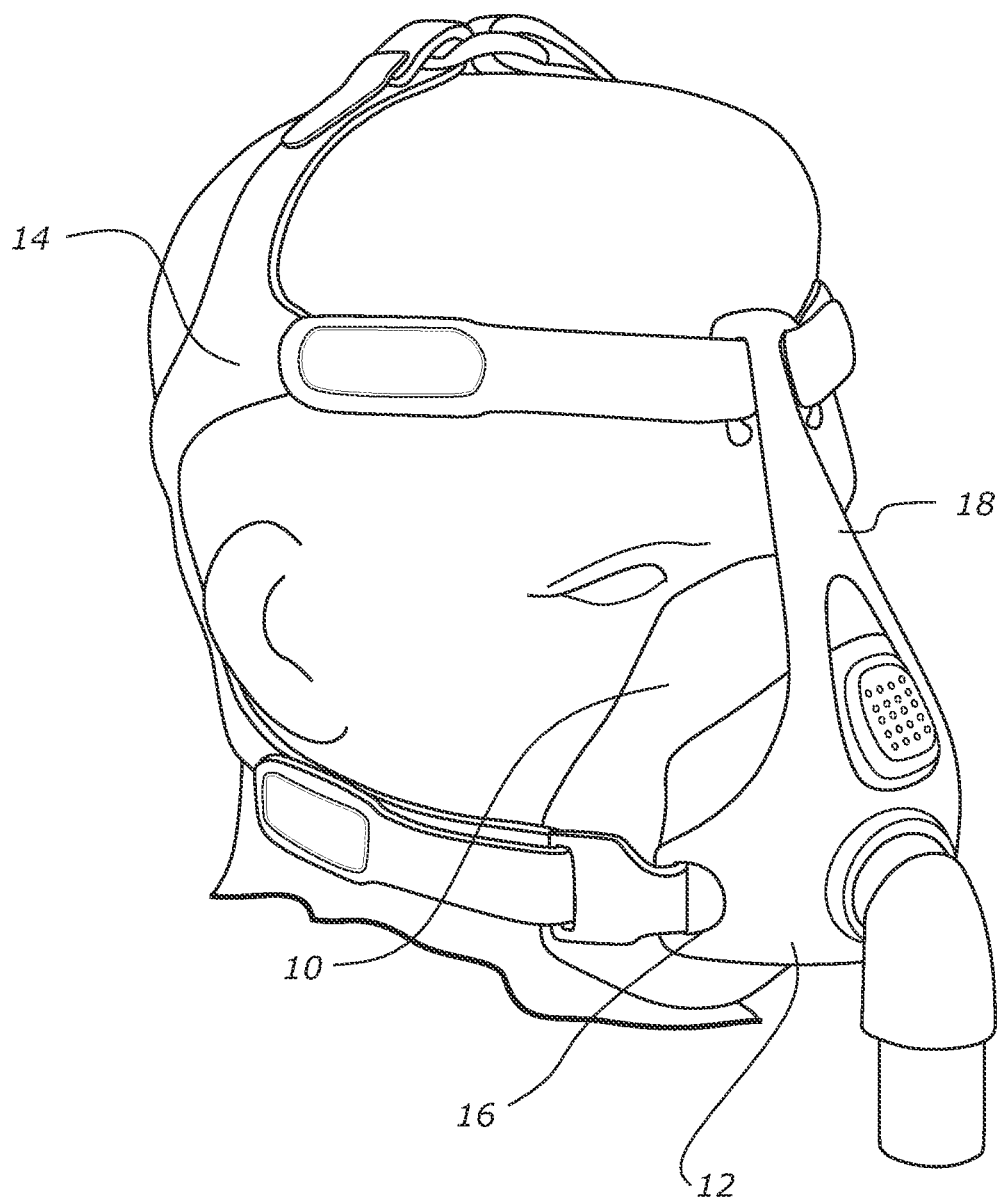
FIG. 1 illustrates a perspective view of a full face headgear assembly and full face interface.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" may refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. The terms "horizontal" and "vertical" are used relative to the interface or headgear assembly properly positioned on a user with the user's head in an upright orientation unless otherwise noted or made clear by the context of the disclosure. The term "horizontal" can refer to a line which is parallel or substantially parallel to the sagittal axis. The term "horizontal" can refer to a line which is parallel or substantially parallel to the anteroposterior axis (dorsoventral). The term "horizontal" can refer to a direction which is perpendicular to the coronal or frontal plane. The term "vertical" can refer to a line which is parallel or substantially parallel to the longitudinal axis. The term "vertical" can refer to a line which is parallel or substantially parallel to the craniocaudal axis. The term "vertical" can refer to a line which is perpendicular to the transverse plane. Moreover, terms such as "first," "second," "third," and so on may be used to describe separate components. Such terminology may include the words specifically mentioned above, derivatives thereof, and words of similar import.

As used herein the term "semi-rigid" shall refer to the ability of a headgear or material to resist stretching relative to the loads to which it may be subjected. Thus, a component such as a side arm may be semi-rigid in one or more directions and may be less rigid in one or more other directions. In some configurations, the side arm is configured to be substantially rigid in a width or vertical direction, in use. In some configurations, the side arm is configured to be substantially rigid in a lengthwise, longitudinal or horizontal direction, in use. In some configurations, the side arm is configured to be less rigid in a third direction, such as a thickness direction or toward and away from the cheeks of the user, in use. The third direction can be along the left-right axis (frontal axis). This flexibility in one direction allows the headgear assemblies to conform to a user's head while providing rigidity in a direction that stabilizes and minimizes dislodging of the interface on a user's face. A semi-rigid side arm, for example, can resist stretching that would loosen or stretch one or more straps during use and/or shift the placement of the respiratory interface relative to the user.

FIG. 1 illustrates an example of a full-face headgear assembly and full-face interface. Full-face headgear assemblies typically require upper and lower headgear connection points to provide the sufficient retention forces in the appropriate directions. The upper and lower headgear connection points are required in order to achieve an effective seal between the full-face interface and a user's face. Typically, the headgear assembly requires four points of adjustment or connection to the full-face interface as shown in FIG. 1.

The full-face headgear assembly and full-face interface is configured to provide a supply of pressurized breathable gases to a patient's airway. The full-face headgear assembly 14 is connected to a frame 12. The frame 12 is part of the interface and comprises a substantially triangular component having two lower headgear connections 16 (forming the lower points of the triangle) and a forehead support 18 (forming the upper point of the triangle). The forehead support 18 comprises an elongate member that in use extends upwardly, away from the headgear connections 16, towards the patient's forehead. The headgear assembly 14 also comprises one more headgear straps that are configured to extend around and retains the interface 10 on the patient's head, in use.

The interface can include a sealing cushion comprising an integrally formed seal housing and flexible cushion. The frame 12 further comprises a sealing cushion connection to couple to the sealing cushion 10. The seal housing is configured to provide a substantially rigid breathing chamber about the patient's nose and/or mouth. In the embodiment shown in FIG. 1, the sealing housing is configured to attach to the sealing cushion connection of the frame 12. The flexible cushion is configured to engage a patient's face such that a substantially airtight seal is formed about the patient's nose, mouth or nose and mouth. The flexible cushion can be made from silicone, thermoplastic elastomer or any other appropriate material capable of at least partially conforming to the facial geometry of the patient. In the embodiment shown in FIG. 1, the flexible cushion comprises a rolling bridge located proximal to the patient's nasal bridge, in use. The rolling bridge is configured to allow an upper portion of the flexible cushion to roll during hinging movement of the upper portion relative to a lower portion of the flexible cushion. The interface is configured to seal around the nose and mouth. In some embodiments, the interface seals only around or under the user's nose. In some embodiments, the interface seals only around or in the user's mouth.

Typically, full-face headgear assemblies are cumbersome and complicated, due in part to the plurality of straps, connection points, and adjustable parts. These headgear assemblies are typically difficult to put on (don) and take off (doff). As one example, the headgear assembly shown in FIG. 1 includes lower side straps that are positioned below a user's ears in use. The lower side straps either have to be disconnected during fitting of the full-face interface or the lower side straps have to be pulled over the user's ears which can cause discomfort.

As shown in FIG. 1, forehead supports or T-pieces are common in full-face headgear assemblies. The forehead support can make the full-face headgear assembly intrusive and claustrophobic for users. However, there are tradeoffs with removing the forehead support. Without the forehead support, the full-face interface has a tendency to ride up the user's face. The headgear assembly preferably therefore provides force vectors that counteract this movement if the forehead support is removed.

In addition, these headgear assemblies have a steep learning curve to master, including the ability to tighten and adjust each strap. Adjustment mechanisms require user interaction and, as a result, are prone to misuse or maladjustments including over-tightening. In some cases, adjustment of the headgear assembly can be difficult and time-consuming. As disclosed herein, there is an opportunity to simplify headgear assemblies and improve the ease of use.

Figure 2A:
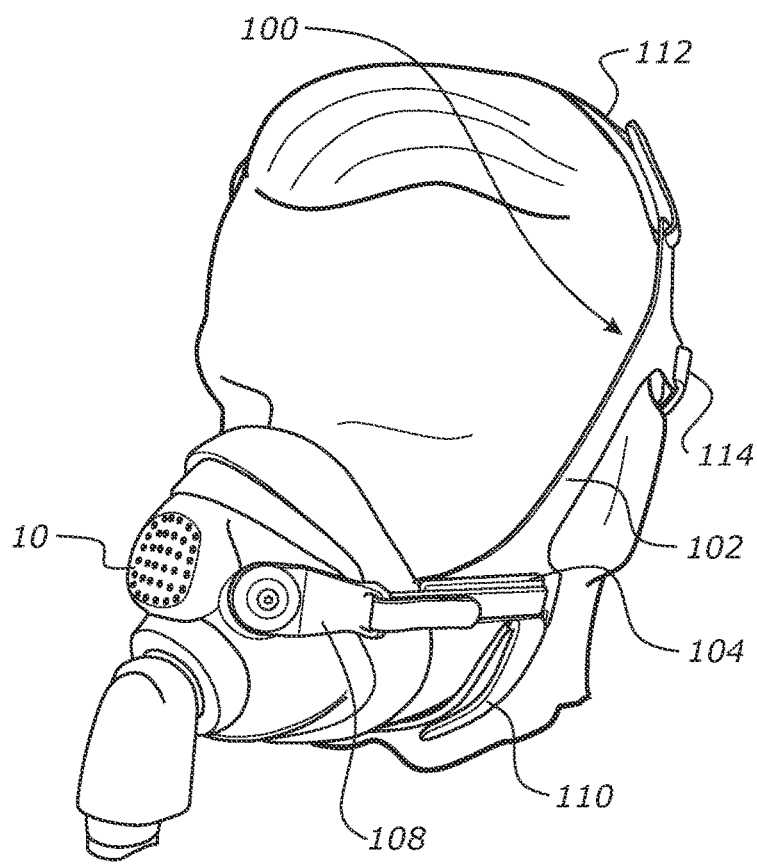
FIG. 2A illustrates a perspective view of a user, a headgear assembly, and an interface.
Figure 2B:
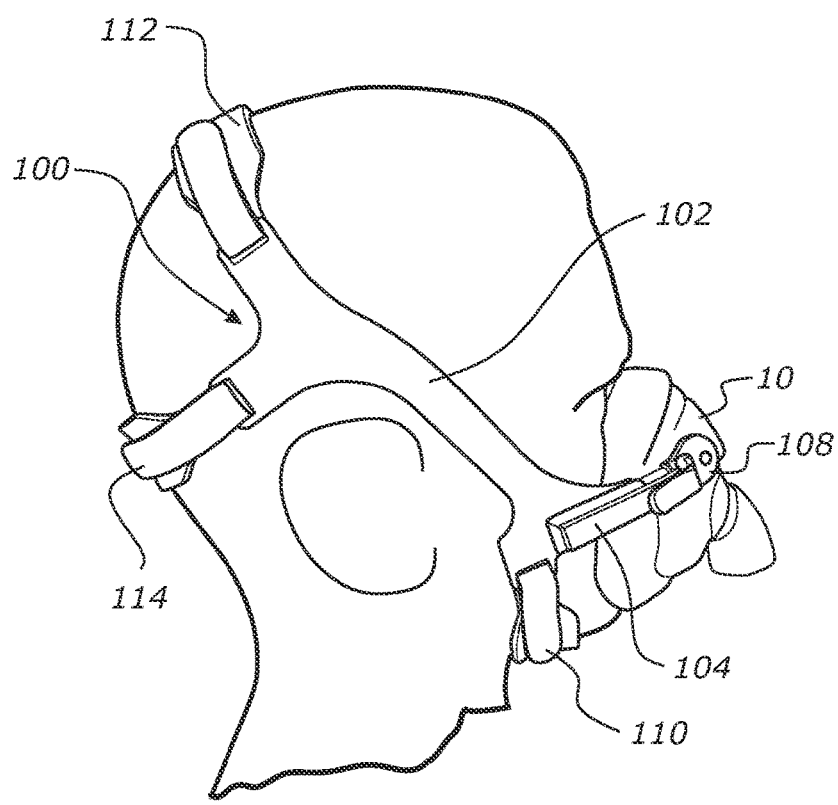
FIG. 2B illustrates a side view of the user, the headgear assembly, and the interface of FIG. 2A.

FIG. 2A illustrates an interface 10 and a headgear assembly 100 including semi-rigid side arms 102 that are pivotally connected to the full-face interface 10, as described herein. The headgear assembly 100 can be used with any interface 10 including an under-nose full-face interface and over-nose full-face interface. FIG. 2B illustrates a side view of FIG. 2A.

Figure 3:
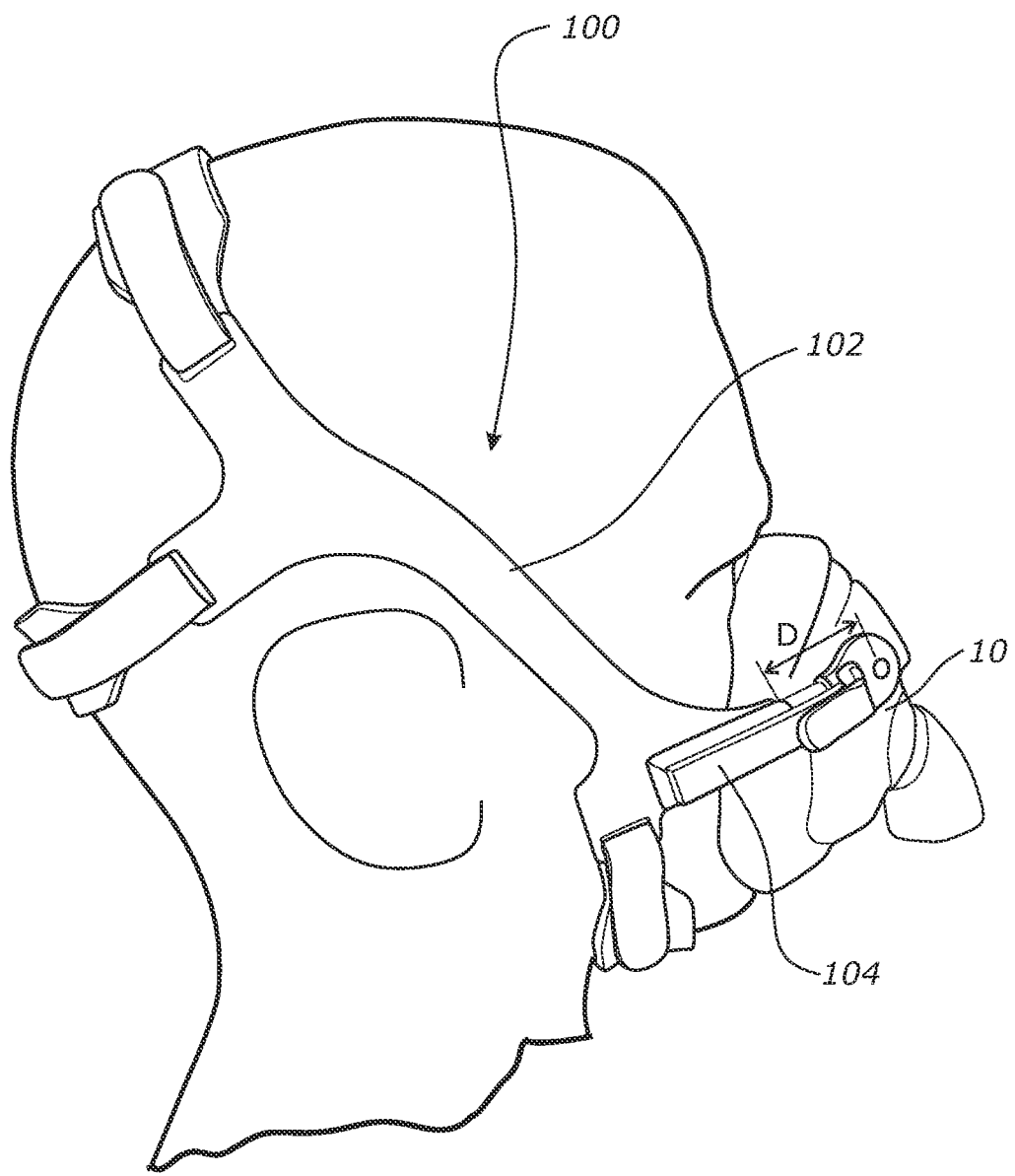
FIG. 3 illustrates a side view of the user, the headgear assembly, and the interface of FIG. 2A.

The headgear assembly 100 includes a pair of opposing, semi-rigid side arms 102. In use, the semi-rigid side arms 102 are placed such that one side arm 102 is on each side of the head of the user. The headgear assembly 100 includes an adjustment mechanism 104 that provides adjustability between the headgear assembly 100 and the interface 10. The adjustment mechanism 104 can adjust the distance between the side arm 102 and the interface 10 a distance "D" as shown in FIG. 3. The headgear assembly 100 includes connecting members 108 that provide the pivotal connection. Each side arm 102 couples to a connecting member 108 which couples to the interface 10.

The headgear assembly 100 can include one or more straps. The headgear assembly 100 includes a chin strap 110 that extends under the user's chin in use. The headgear assembly 100 includes a top strap 112 that extends over the top or crown of a user's head in use. The headgear assembly 100 includes a rear strap 114 that extends around the rear of a user's head in use.

Figure 4A:
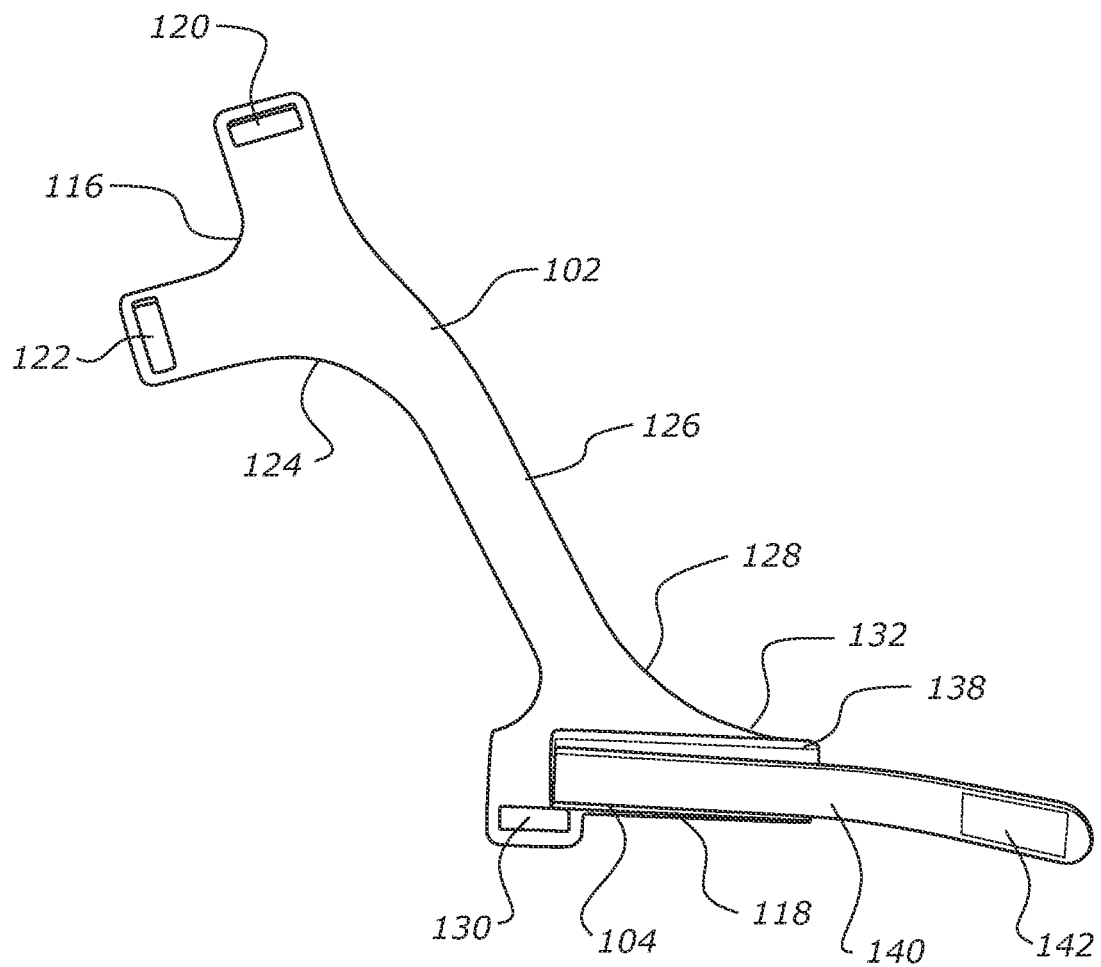
FIG. 4A illustrates a side view of a side arm of the headgear assembly of FIG. 2A.

FIG. 4A illustrates the side arm 102. The side arm 102 includes an upper end 116 and a lower end 118. The upper end 116 is bifurcated to form a top strap connection point 120 and a rear strap connection point 122. The top strap connection point 120 and the rear strap connection point 122 form an angle there between. The angle can be approximately 90 degrees (e.g., 70 degrees, 80 degrees, 90 degrees, 100 degrees, 110 degrees, etc.). The top strap connection point 120 is substantially vertical and the rear strap connection point 122 is substantially horizontal. The side arm 102 includes an ear arch 124. The ear arch 124 passes above the ear of the user in use. The side arm 102 includes a mid-section 126 between the upper end 116 and the lower end 118. The side arm 102 includes a cheek curve 128. The cheek curve 128 passes near the cheekbone of the user in use. The cheek curve 128 is concave. The cheek curve 128 is concave toward the eyes of the user. The cheek curve 128 provides a smooth curve between the mid-section 126 and the lower end 118 of the side arm 102. The cheek curve 128 slopes downward toward the lower end 118.

Figure 4B:
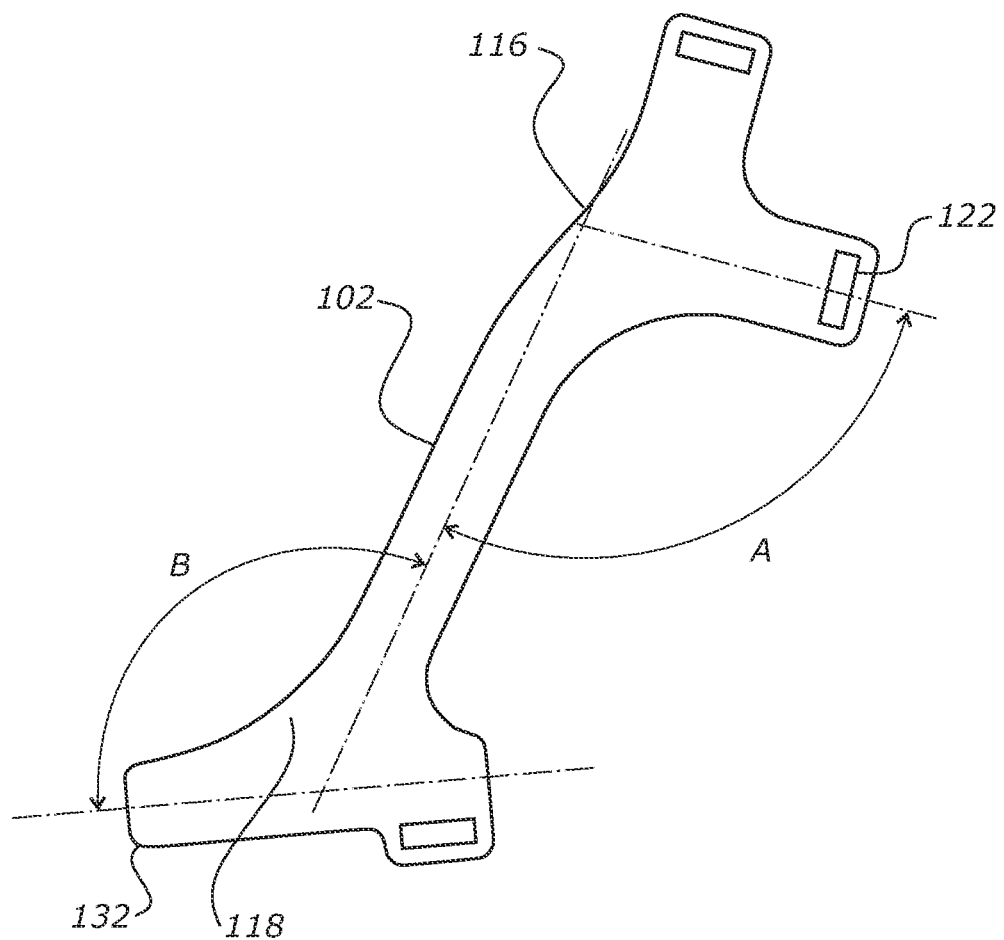
FIG. 4B illustrates a side view of various angles of the side arm of the headgear assembly of FIG. 2A.
Figure 4C:
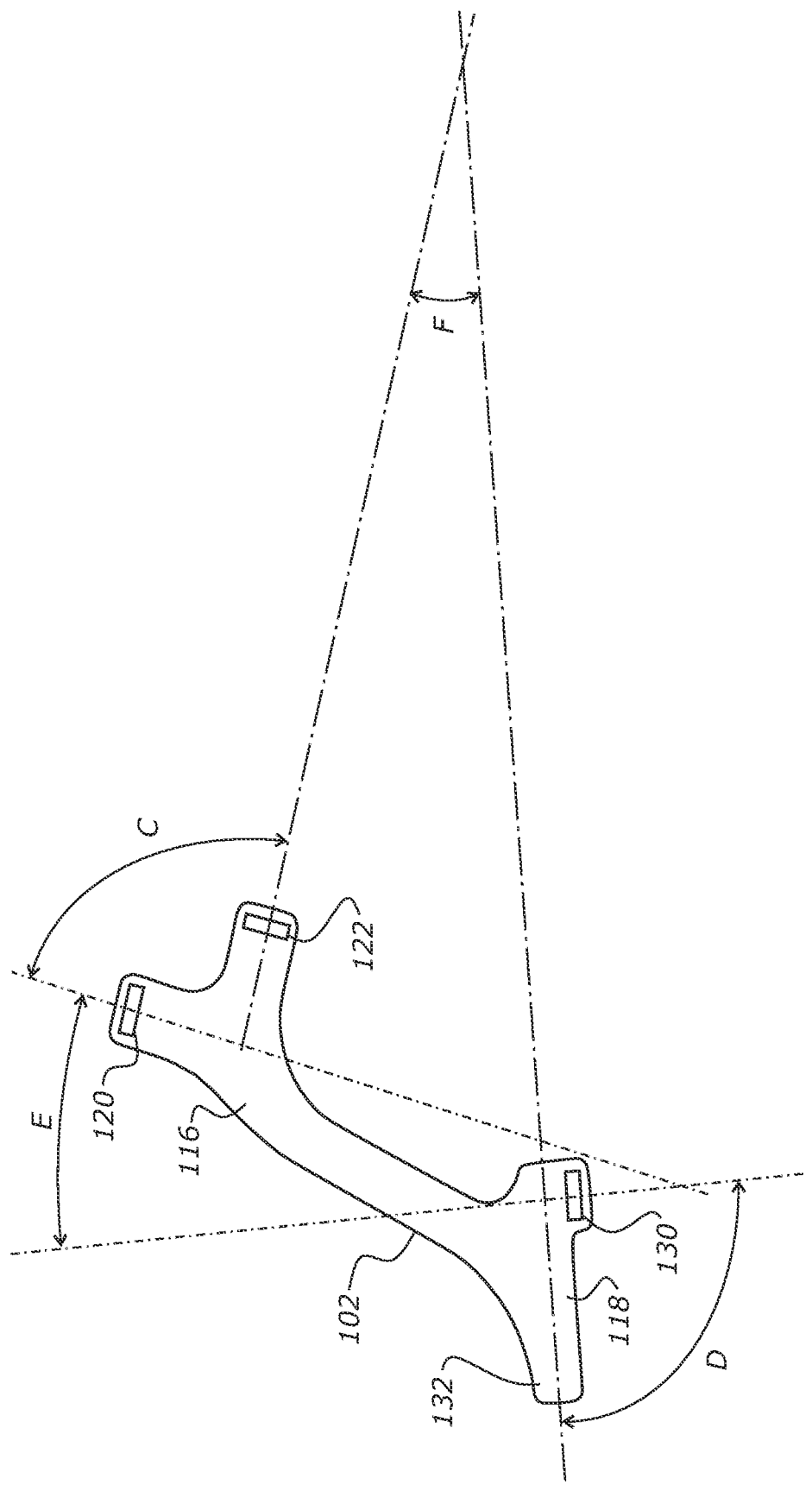
FIG. 4C illustrates a side view of various angles of the side arm of the headgear assembly of FIG. 2A.

The lower end 118 is bifurcated to form a chin strap connection point 130 and a support 132. The chin strap connection point 130 and the support 132 form an angle there between. The angle can be approximately 90 degrees (e.g., 70 degrees, 80 degrees, 90 degrees, 100 degrees, 110 degrees, etc.). The chin strap connection point 130 is substantially vertical and the support 132 is substantially horizontal. The support 132 couples to the adjustment mechanism 104, or a component thereof. The adjustment mechanism 104 includes a female component 138, as described herein. The side arm 102 includes a pull tab 140 and a fastener 142, as described herein. FIG. 4A illustrates the side arm 102 designed to be adjacent to the right side of the user's face during use. The side arm 102 designed to be adjacent to the left side of the user's face during use can include any or all of the features shown in FIG. 4A and can be a mirror image of the illustrated side arm 102. FIGS. 4B and 4C illustrate the side arm adjacent to the left side of the user's face.

As described herein the upper end 116 and the lower end 118 are bifurcated. The side arm 102 includes an elongate body extending between the upper end 116 and the lower 118. While upper and lower are used herein, the upper end 116 and the lower end 118 can be a first end and a second end. The upper end 116 includes a first projection and a second projection which project from the body at the upper end 116. The first projection includes the top strap connection point 120. The second projection includes rear strap connection point 122. The lower end 118 includes a third projection and a fourth projection which project from the body at the lower end 118. The third projection includes the chin strap connection point 130. The fourth projection includes the support 132. Other configurations of the projections are contemplated. Each of the first, second and third projections have a connection portion for connecting the straps of the headgear assembly 100 to the side arm 102. The fourth projection has a connection portion, in the form of the support 132, for connecting the interface 10 to the side arm 102 (via the adjustment mechanism).

In some embodiment, the elongate body of the side arm 102 is thin. The side arm 102 has a constant thickness. In some embodiments, the side arm 102 does not have a constant thickness. The side arm 102 has a thickness between 0.5 mm and 3 mm. The upper end 116 of the side arm 102 has a constant thickness. In some embodiments, the upper end 116 does not have a constant thickness. The upper end 116 of the side arm 102 has a thickness between 0.5 mm and 3 mm. The lower end 118 of the side arm 102 has a constant thickness. In some embodiments, the lower end 118 does not have a constant thickness. The lower end 118 of the side arm 102 has a thickness between 0.5 mm and 3 mm. Each of the projections has a thickness of 0.5 mm and 3 mm. Examples of thicknesses used herein include 0.5 mm, 0.75 mm, 1 mm, 1.25 mm, 1.5 mm, 1.75 mm, 2 mm, 2.25 mm, 2.5 mm. 2.75 mm, and 3 mm, including any range of two or more thicknesses. Other thicknesses are contemplated for the side arm 102, or portions thereof, including 0.25 mm, 3.25 mm, 3.5 mm, 3.75 mm, 4 mm, 4.25 mm, 4.5 mm, 4.75 mm, 5 mm, 5.25 mm, 5.5 mm. 5.75, and 6 mm, including any range of two or more thicknesses. The thickness of the side arm 102 can increase between 0.5 mm and 2 mm if the side arms 102 are intra-moulded. This increase in thickness accounts for the textile thickness. In some embodiments, there is a layer of padding applied to an internal surface of the side arms 102. In some embodiments, the padding is foam, but other materials are contemplated. The thickness of the side arm 102 increases between 0.5 mm and 4 mm if the side arm 102 includes padding. The padding has a thickness between 0.5 mm and 4 mm. Examples of thicknesses of the padding include 0.5 mm, 0.75 mm, 1 mm, 1.25 mm, 1.5 mm, 1.75 mm, 2 mm, 2.25 mm, 2.5 mm. 2.75 mm, 3 mm, 3.25 mm, 3.5 mm, 3.75 mm, and 4 mm including any range of two or more thicknesses. Other thicknesses of the padding are contemplated.

The features of the side arm have substantially constant thickness. The elongate body of the side arm 102 has constant thickness. In some embodiment, the elongate body of the side arm 102 has variable thickness. The upper end 116 of the side arm 102 has constant thickness. In some embodiment, the upper end 116 of the side arm 102 has variable thickness. The lower end 118 of the side arm 102 has constant thickness. In some embodiment, the lower end 118 of the side arm 102 has variable thickness. In some embodiments, the elongate body of the side arm 102 is planar when not in use, but the elongate body of the side arm 102 is curved to match the user's face during use. In use, the lower ends 118 of the headgear assembly 100 curve inwardly toward each other. In some embodiments, the elongate body of the side arm 102 is not planar. In some embodiments, the upper end 116 of the side arm 102 is planar. In some embodiments, the upper end 116 is not planar. In some embodiments, the lower end 118 of the side arm 102 is planar. In some embodiments, the lower end 118 is not planar. In some embodiments, one or more projections including the connection point is planar. In some embodiments, one or more projections including the connection point is not planar. In some embodiments, each projection is planar.

The elongate body of the side arm 102 extends along a longitudinal axis. The first and second projections project from the elongate body at different angles to each other. The first and second projections project from the elongate body at different angles relative to the longitudinal axis. The third and fourth projections project from the elongate body at different angles to each other. The third and fourth projections project from the elongate body at different angles relative to the longitudinal axis. In some embodiments, the first and second projections project from the elongate body at the same angle to each other.

FIG. 4B illustrates various angles of the side arm 102. The side arm 102 includes a longitudinal axis. The side arm 102 includes angle A. The angle A is the angle between the upper end 116 and the longitudinal axis. The angle A is the angle between the second projection and the longitudinal axis. The angle A is the angle between the rear strap connection point 122 and the longitudinal axis. The angle A is 110 degrees. The angle A is between 80 degrees and 150 degrees. Examples of angles include 80 degrees, 90 degrees, 100 degrees, 110 degrees, 120 degrees, 130 degrees, 140 degrees, and 150 degrees, including any range of two or more angles. Other examples of angles for angle A include 50 degrees, 60 degrees 70 degrees, 160 degrees, 170 degrees, and 180 degrees, including any range of two or more angles.

The side arm 102 includes angle B. The angle B is the angle between the lower end 118 and the longitudinal axis. The angle B is the angle between the fourth projection and the longitudinal axis. The angle B is the angle between the support 132 and the longitudinal axis. The angle B is 120 degrees. The angle B is between 90 degrees and 140 degrees. Examples of angles include 90 degrees, 100 degrees, 110 degrees, 120 degrees, 130 degrees, and 140 degrees, including any range of two or more angles. Other examples of angles for angle B include 50 degrees, 60 degrees 70 degrees, 80 degrees, 150 degrees, 160 degrees, 170 degrees, and 180 degrees, including any range of two or more angles.

FIG. 4C illustrates various angles of the side arm 102. The angle C is the angle between the first projection and the second projection. The angle C is the angle between the top strap connection point 120 and the rear strap connection point 122. The angle C is 90 degrees. The angle C is between 80 degrees and 120 degrees. Examples of angles for angle C include 80 degrees, 90 degrees, 100 degrees, 110 degrees, and 120 degrees, including any range of two or more angles. Other examples of angles for angle C include 50 degrees, 60 degrees, 70 degrees, 130 degrees, 140 degrees, 150 degrees, 160 degrees, 170 degrees, and 180 degrees, including any range of two or more angles.

The angle D is the angle between the third projection and the forth projection. The angle D is the angle between the chin strap connection point 130 and the support 132. The angle D is 90 degrees. The angle D is between 80 degrees and 120 degrees. Examples of angles for angle D include 80 degrees, 90 degrees, 100 degrees, 110 degrees, and 120 degrees, including any range of two or more angles. Other examples of angles for angle D include 50 degrees, 60 degrees, 70 degrees, 130 degrees, 140 degrees, 150 degrees, 160 degrees, 170 degrees, and 180 degrees, including any range of two or more angles.

The angle E is the angle between the first projection and the third projection. The angle E is the angle between top strap connection point 120 and the chin strap connection point 130. The angle E is 20 degrees. The angle E is between 0 degrees and 40 degrees. Examples of angles for angle E include 0 degrees, 10 degrees, 20 degrees, 30 degrees, and 40 degrees, including any range of two or more angles. Other examples of angles for angle E include 50 degrees, 60 degrees, 70 degrees, 80 degrees, 90 degrees, 100 degrees, 110 degrees, 120 degrees, and 130 degrees, including any range of two or more angles. The first and third projections project away from the elongate body in substantially opposed directions.

The angle F is the angle between the second projection and the fourth projection. The angle F is the angle between rear strap connection point 122 and the support 132. The angle F is 20 degrees. The angle F is between 0 degrees and 40 degrees. Examples of angles for angle F include 0 degrees, 10 degrees, 20 degrees, 30 degrees, and 40 degrees, including any range of two or more angles. Other examples of angles for angle F include 50 degrees, 60 degrees, 70 degrees, 80 degrees, 90 degrees, 100 degrees, 110 degrees, 120 degrees, and 130 degrees, including any range of two or more angles. The second and fourth projections project away from the elongate body in substantially opposed directions.

The side arms 102 are configured to extend between the interface 10, across a user's cheeks to a point above the user's ears where the top strap 112 and the rear strap 114 are connected thereto. The side arms 102 are semi-rigid and planar. The side arms 102 are able to flex in a direction that is into the page of FIG. 4, or towards the user's cheeks, in use. The side arms 102 resist bending in a vertical direction and/or a horizontal direction in use. The side arms 102 are made from a plastic material. In some embodiments, the side arms 102 are not made from a plastic material.

The semi-rigid material of the side arms 102 provides structure to the headgear assembly 100. The side arms 102 transfer forces to the top strap 112 and the rear strap 114. The side arms 102 resist rotation of the interface 10 on the user's face. The side arms 102 enable a single connection point between the headgear assembly 100 and each side of the interface 10. The side arms 102 transfer and direct forces from the interface 10 to the top strap 112 and the rear strap 114 of the headgear assembly 100.

As described herein, the upper end 116 of the side arm 102 is bifurcated to provide connection points for the top strap 112 and the rear strap 114. The upper end 116 includes the top strap connection point 120 that directs the top strap 112 toward a respective direction (e.g., around the crown of the user's head). The upper end 116 includes the rear strap connection point 122 that directs the rear strap 114 toward a respective direction (e.g., around the back of the user's head). The top strap connection point 120 and rear strap connection point 122 include apertures through which the top strap 112 and the rear strap 114 can pass. The side arm 102 is curved to form the ear arch 124 that is designed to sit above a user's ear in use. The ear arch 124 avoids contact with top of user's ears to avoid discomfort.

With reference to the orientation of FIG. 4, the side arm 102 curves downwards in a left to right direction to pass between a user's temple and the user's ear. The side arm 102 curves downward in a left to right direction to pass across their cheeks to the lower end 118. The side arm 102 includes the cheek curve 128. The lower end 118 extends at an angle from the mid-section 126 of the side arm 102 so that the lower end 118 extends across the user's cheek in use. The lower end 118 can be positioned horizontal in use when the user is upright. The lower end 118 is closer to horizontal in comparison to the mid-section 126. If not exactly horizontal, then the lower end 118 can be angled slightly upward as shown in FIG. 4 or angled slightly downward, depending on user facial and/or cranial geometry. The horizontal or substantially horizontal lower end 118 helps to counteract blow-off forces that act in a direction that is perpendicular to the user's face. The lower end 118 includes the chin strap connection point 130. The chin strap connection point 130 includes an aperture through which a lateral end of the chin strap 110 can pass.

Figure 5A:
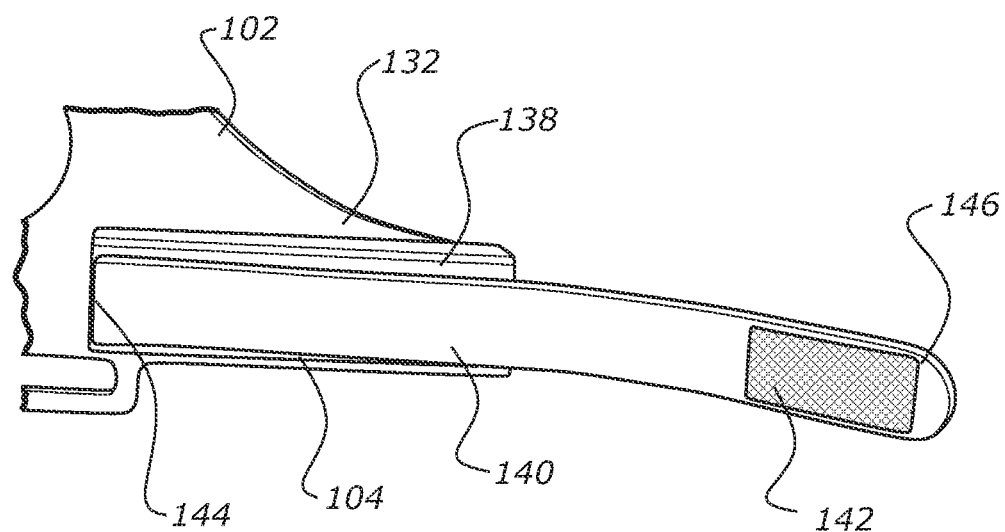
FIG. 5A illustrates a side view of a female component of an adjustment mechanism of the headgear assembly of FIG. 2A.
Figure 5B:
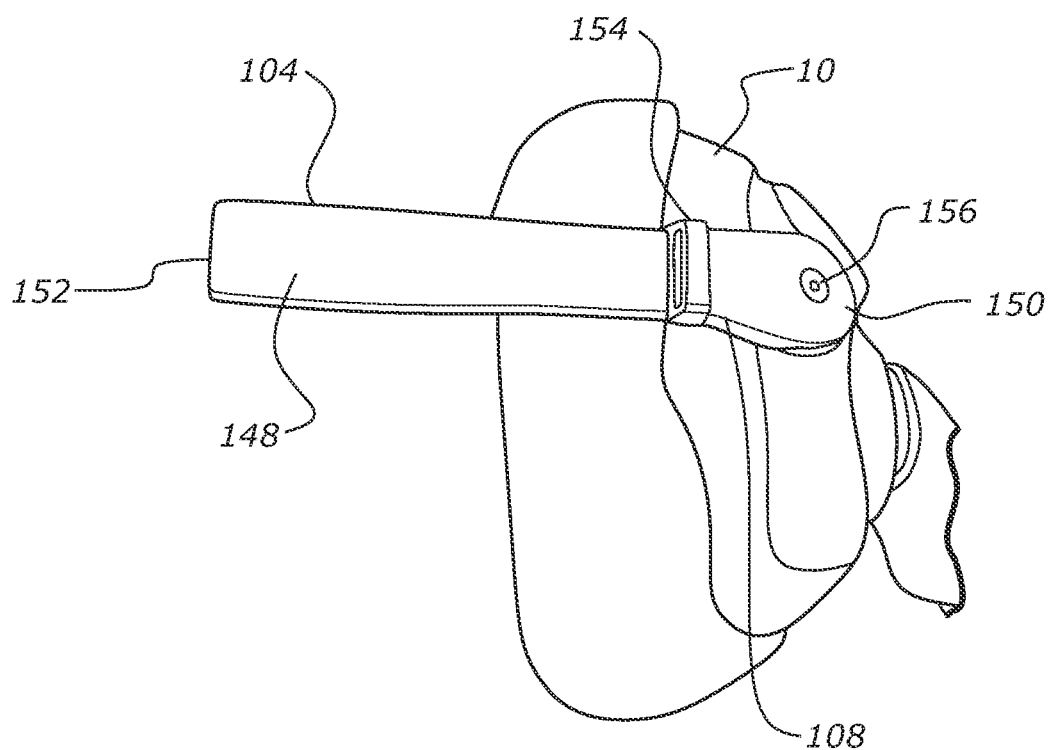
FIG. 5B illustrates a side view of a male component of the adjustment mechanism of the headgear assembly and the interface of FIG. 2A.

FIGS. 5A and 5B illustrate components of the adjustment mechanism 104. FIG. 5A illustrates a portion of the side arm 102. The side arm 102 couples to the adjustment mechanism 104. The support 132 includes a forward portion of the lower end 118 of the side arm 102. The support 132 couples to the female component 138 of the adjustment mechanism 104. The pull tab 140 couples to the female component 138 at a fixed end 144. The pull tab 140 includes the fastener 142 near a free end 146 of the pull tab 140.

FIG. 5B illustrates additional components of the adjustment mechanism 104. The adjustment mechanism 104 includes a male component 148. The male component 148 is designed to slide within the female component 138 to provide an adjustment between the headgear assembly 100 and the interface 10.

Some embodiments disclosed herein involve a headgear assembly 100 that upon fitment to the head of a user automatically adjusts to the correct size and, once in use, transforms in properties from an elasticated "stretchy" strap/strapping to an "inelastic" strap/strapping. In some configurations, the headgear assembly 100 (alone or as integrated in an interface assembly 10, 100) exhibits a relatively small contraction force that tends to shorten the headgear assembly 100. When coupled to an interface 10, the headgear assembly 100 and interface 10 cooperate to define a perimeter of the interface assembly 10, 100, which is reduced in length as a result of the contraction force toward a minimum perimeter length. Although not likely to be perfectly circular, the perimeter length is often referred to as a "circumference." Thus, with such an arrangement, the interface assembly 10, 100 can be positioned on the user's head and will automatically contract to or very near a proper head size, in a manner similar to an elasticated or "stretchy" headgear. The contraction or retraction force preferably is sufficient to support the weight of the interface assembly 10, 100 and at least substantially keep the interface assembly 10, 100 in place on the user's head at the smallest head size or minimum useful perimeter length of the interface assembly 10, 100, which may or may not coincide with the minimum perimeter length. In some configurations, the contraction force can be between about 0.5 Newtons and about 5.2 Newtons, or between about 1 Newton and about 2.6 Newtons, or between about 1 Newton and about 1.5 Newtons, including any value and sub-range within these ranges. In other configurations, the contraction force may be insufficient to support the weight of the interface and may require manual assistance to move the interface to a sealed position on the user's face. However, preferably, once the headgear assembly 100 is sufficiently contracted, it is then held in place by, for example, directional lock(s). In some configurations, the contraction force is only sufficient or is configured to support the weight of the headgear assembly 100.

However, in at least some configurations, the contraction force is less than is necessary to maintain the interface 10 in sealed contact with the user's face during treatment/use. That is, the contraction force, alone, cannot resist the blow-off force. In some configurations, the contraction force is insufficient to resist the blow-off force throughout a range of usable perimeter lengths or headgear sizes. Therefore, the headgear assembly 100 and/or interface assembly 10, 100 also exhibits an inelastic behavior in response to forces tending to elongate the headgear assembly 100 or increase the perimeter length of the interface assembly 10, 100. The headgear assembly 100 and/or interface assembly 10, 100 can have a locked mode that can produce a locking force tending to resist expansion, elongation or lengthening of the perimeter length. The locking force can be sufficient to resist elongation, or at least any significant elongation, of the perimeter length in response to blow-off forces. In some configurations, the locking force is sufficient to resist elongation in response to the highest blow-off forces expected with a variety of uses or treatments (e.g., Bi-Level or CPAP, NIV, etc.). In some configurations, the locking force may be selected for one or more particular uses/therapies, but may not be suitable for all uses/therapies. In some configurations, the locking force may be selected to resist elongation in response to forces in addition to blow-off forces, such as hose pull forces, for example.

In some configurations, the headgear assembly 100 and/or interface assembly 10, 100 also exhibits a yield force, above which expansion or elongation of the perimeter length is permitted. Preferably, the yield force is greater than the expected blow-off force. In some configurations, the yield force is greater than the expected blow-off force and the hose pull force. Thus, such a headgear assembly 100 and/or interface assembly 10, 100 has a reserve. Preferably, the yield force is set low enough that a user can at least relatively conveniently apply an elongation force to the headgear assembly 100 and/or interface assembly 10, 100 sufficient to exceed the yield force in order to permit the interface assembly 10, 100 to lengthen and to be applied to the user's head. As described above, the contraction force reduces the perimeter length toward a proper head size.

In some configurations, the headgear assembly 100 and/or interface assembly 10, 100 automatically transitions between a contraction mode, a locked mode and a yield mode in response to the presence or absence of external forces. For example, the headgear assembly 100 and/or interface assembly 10, 100 moves toward or to the minimum perimeter length in the absence of external lengthening or expanding forces. A lengthening or expansion force that is greater than the yield force can be applied to increase the perimeter length of the headgear assembly 100 and/or interface assembly 10, 100 to a length sufficient to permit the interface assembly 10, 100 to be positioned on the user's head. Once the lengthening or expansion force is removed (or reduced to below the contraction force), the contraction force acts to automatically reduce the perimeter length to or substantially to the proper head size such that the interface assembly 10, 100 is supported on the user's head. Upon the start of treatment (application of blow-off force) and/or application of hose pull force, the headgear assembly 100 and/or interface assembly 10, 100 automatically transforms to the locked mode to resist elongation, or at least resist any significant elongation, or increase of the perimeter length. At the end of treatment, or at any time as desired, a force above the yield force can be applied to the headgear assembly 100 and/or interface assembly 10, 100 to increase the perimeter length and permit removal of the interface assembly 10, 100 from the user's head.

Advantageously, with such an arrangement, micro-adjustments of the perimeter length of the headgear assembly 100 and/or interface assembly 10, 100 can be accomplished quickly and conveniently. For example, during treatment or use, the interface 10 can be manipulated to effect micro-adjustment of the perimeter length. For instance, in the event of a leak between the interface 10 and the user's face, the interface 10 can be wiggled or otherwise moved to effect a micro-adjustment of the perimeter length to address the leak. In some cases, the seal of the interface 10 may be compressed against the user's face, which can allow the contraction force to automatically reduce the perimeter length. Upon release of the interface 10, the headgear assembly 100 and/or interface assembly 10, 100 locks at, or very near, the reduced perimeter length. Thus, such configurations permit the headgear assembly and/or interface assembly 10, 100 to micro-adjust, or move to an adjusted perimeter length, as a result of small manipulations (e.g., wiggling) of the interface 10. Manipulation of other portions of the interface assembly 10, 100 (e.g., headgear assembly 100 or breathing tube/gases conduit) can similarly result in micro-adjustment. Because of the nature of the human head and/or the conditions under which interface assemblies 10, 100 are used, quick and convenient micro-adjustment can dramatically improve performance and user satisfaction of an interface assembly 10, 100. Treatment often occurs at night and/or under other situations when the user is lying down. Thus, the headgear assembly 100 can be in contact with surface, such as a pillow or bed. Movement of the user's head relative to such surfaces can cause movement of the headgear assembly 100, which can alter the fit of the headgear assembly 100. For example, hair can move or "compress" beneath the headgear assembly 100, which can alter the fit. The headgear straps may move up, down or rotationally on the head, which can alter the fit. Such alterations in fit can result in leaks between the interface 10 and the user's face. The above-described adjustment technology can permit such changes in fit to be addressed automatically or with small manipulations of the interface 10 or other portions of the interface assembly 10, 100. Moreover, the interface assembly 10, 100 can be removed and reapplied and automatically adjust to at or very near a proper headgear size. In contrast, if conventional non-stretch headgear is moved from its desired adjustment position, such as by mistake or as a result of cleaning, it can be difficult and time-consuming to re-establish the desired adjustment position. Conventional elasticated headgear addresses the adjustment issue, but because the contraction force must resist the highest expected blow-off and hose pull forces at the smallest useable headgear size, elasticated headgear applies a relatively large pressure to the user's head that is only partially relieved by the application of blow-off force. Such pressure may be substantial for a user with a relatively large head size and low treatment pressure.

The connecting member 108 provides the connection between the headgear assembly 100 and the interface 10. The connecting member 108 includes or is formed as a single piece with the male component 148 of the adjustment mechanism 104. The connecting member 108 includes a front end 150 and a rear end 152. The male component 148 is located near the rear end 152 of the connecting member 108. The connecting member 108 includes a rotational adjustment mechanism or pivot connection 156. The pivot connection 156 is located near the front end 150 of the connecting member 108.

In use, the male component 148 is inserted into the female component 138 of the adjustment mechanism 104. The male component 148 is inserted into the female component 138 in a telescoping manner. In some methods of use, the interface 10 slides toward the face of the user as the male component 148 slides further within the female component 138. The connecting member 108 includes a pull tab loop 154. The pull tab 140 couples to the female component 138 as shown in FIG. 5A. The free end 146 of the pull tab 140 is passed through the pull tab loop 154. The user can pull the free end 146 to move the headgear assembly and the interface 10 toward each other. The pull tab 140 is designed to pass through and around the pull tab loop 154 such that the fastener 142 can be secured upon sufficient tightening of the adjustment mechanism 104. The pull tab 140 limits or prevents further extension movement of the adjustment mechanism 104 once the fastener 142 is secured.

Figure 6A:
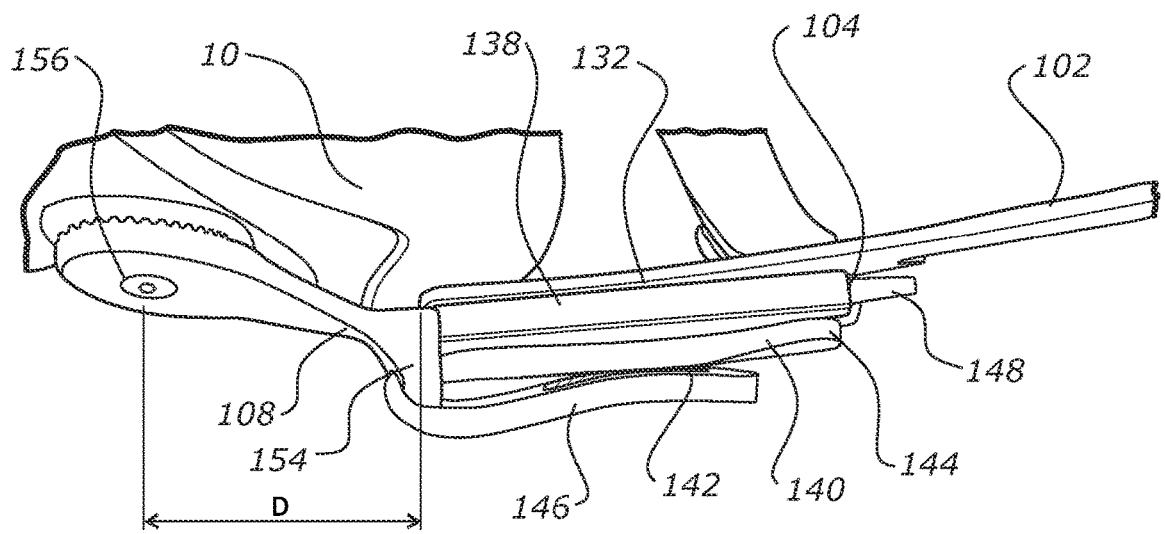
FIG. 6A illustrates a top view of a retracted configuration of the adjustment mechanism of the headgear assembly and the interface of FIG. 2A.
Figure 6B:
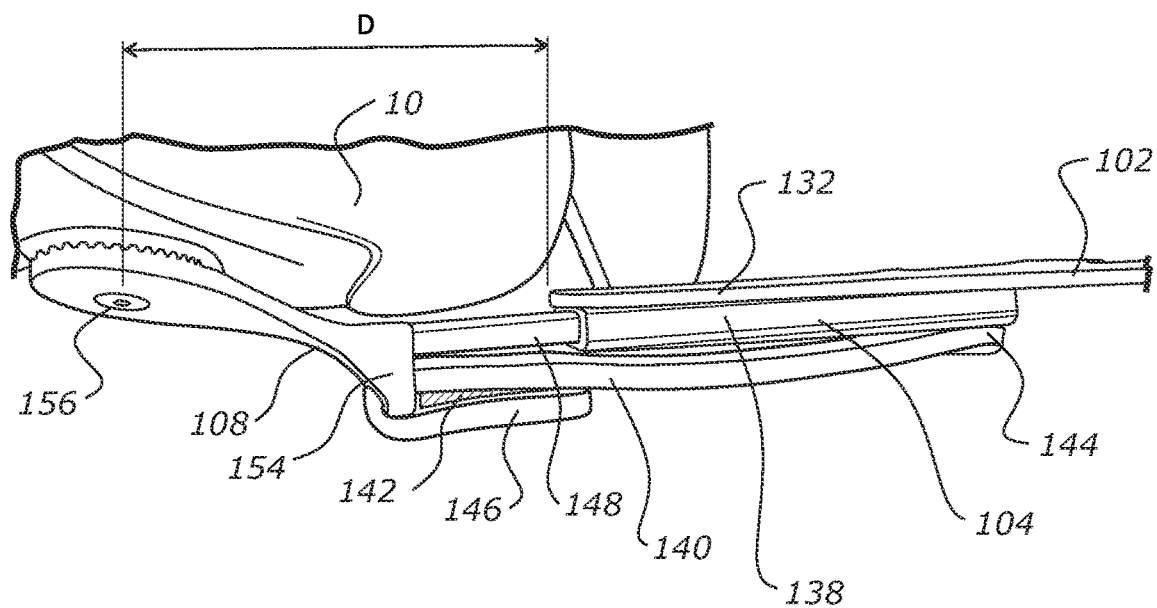
FIG. 6B illustrates a top view of an extended configuration of the adjustment mechanism of the headgear assembly and the interface of FIG. 2A.

FIG. 6A illustrates a top view of a retracted configuration of the adjustment mechanism 104. FIG. 6B illustrates a top view of an extended configuration of the adjustment mechanism 104. The distance "D" is illustrated as a measurement between the pivot connection 156 and a location (e.g., the front edge) on the female component 138. In the retracted configuration, the side arm 102 is closer to the interface 10. In the extended configuration, the side arm 102 is farther from the interface 10.

FIGS. 6A and 6B illustrate the connecting member 108 including the pull tab loop 154 and the pivot connection 156, the female component 138 and the male component 148 of the adjustment mechanism 104, and the pull tab 140. In both the retracted configuration and the extended configuration, the pull tab 140 secures the side arm 102 to the connecting member 108 to maintain the configuration. In the retracted configuration, the male component 148 is mostly or completely housed within the female component 138 and the interface 10 is close to the user's face and/or headgear assembly 100. In an extended configuration, the male component 148 partially protrudes from the front end of the female component 138 so that the interface 10 is spaced away from the user's face and/or headgear assembly 100. In the retracted configuration there is more overlap between the female component 138 and the male component 148 relative to the extended configuration.

The adjustment mechanism 104 is configured to adjustably position the interface 10 relative to the headgear assembly 100 by adjusting a distance "D" between the pivot connection 156 and the side arm 102. The adjustment mechanism 104 includes the male component 148 coupled to or formed with the connecting member 108. The connecting member 108 is located at a front end of the male component 148 or, as described above, can be unitarily formed with the male component 148. The male component 148 is slideably engaged with or received by the female component 138 at a rear end. The male component 148 or connecting member 108 also includes the pull tab loop 154 that protrudes from an outer surface adjacent the pivot connection 156 at the front end. The pull tab loop 154 is configured to receive the free end 146 of the pull tab 140 as shown in FIGS. 6A and 6B.

The adjustment mechanism 104 includes the female component 138, which is coupled to or formed with the side arm 102. The female component 138 comprises a housing that is configured to receive the male component 148 in a sliding or telescopic manner. The female component 138 has a rectangular housing. In some embodiments, the female component has any shaped housing. The housing of the female component 138 has any cross-sectional shape (e.g., round, circular, elliptical, polygonal, triangular, etc.). The female component 138 is attached to the support 132 of the side arm 102. The female component 138 is integrally formed with the side arm 102. In some embodiments, the female component 138 is not integrally formed with the side arm 102. The pull tab 140 is connected to an outer surface of or another suitable location on the female component 138. The pull tab 140 comprises an elongate piece of flexible material. In some embodiments, the pull tab 140 is made of non-flexible material. The pull tab 140 includes the fixed end 144 attached to the rear end of the female component 138 and the opposing, free end 146. The free end 146 includes the fastener configured to secure the adjustment mechanism 140. The fastener 142 is a hook component of a hook and loop fastener that is configured to secure the free end 146 of the pull tab 140 to another part of the pull tab 140, which forms the loop component of the hook and loop fastener. In some embodiments, the fastener 142 is any other type of fastener. The pull tab 140 can limit further movement of the male component 148 relative to the female component 138.

The pull tab 140 is configured to pass through the pull tab loop 154, be folded back over onto itself, and fastened into place by the fastener 142. In some methods of use, the user pulls on the free ends 146 of the pull tabs 140 either rearward towards the user's face, in use, or laterally away from the user's face. Pulling the free ends 146 of the pull tabs 140 will cause the male component 148 to be pulled towards the female component 138, thus increasing the overlap between the male component 148 and the female component 138. The male component 148 telescopes within the female component 138. Pulling the free ends 146 of the pull tabs 140 will tighten the fit of the interface 10 with the user's face. The user can secure the fastener 142 once the desired fit is achieved. To loosen the fit of the interface 10, the fastener 142 can be released and the interface 10 pulled away from the user's face. The spring force within the compressed seal of the interface 10 may cause the interface 10 to be pushed away from the user's face when the fastener 142 is released. The pull tab 140 is made from Breathoprene™ or another suitable textile and foam laminate. In some embodiments, the pull tab 140 is made from any other suitable material. The pull tab 140 is preferably non-stretch. In some embodiments, the pull tab 140 has some elasticity.

The male component 148 and the female component 138 comprise different materials. In some embodiments, the male component 148 and the female component 138 comprise the same material. The male component 148 and the female component 138 comprise materials that reduce friction and binding between the male component 148 and the female component 138. The male component 148 and the female component 138 of the adjustment mechanism 104 are substantially rigid and straight in order to enable linear sliding and minimize binding during adjustment. The male component 148 and the female component 138 are horizontal in use. The male component 148 and the female component 138 provide adjustment in the direction of blow-off forces.

The male component 148 and the female component 138 of the adjustment mechanism 104 provide rigidity between the side arm 102 and the interface 10. The use of a rigid or semi-rigid adjustment mechanism 104 can be beneficial in applications in which the force vectors between the pressurized interface seal and the headgear assembly are not aligned. This misalignment in force vectors results in a situation where moments are generated, which can be at least partially counteracted through the rigidity within the headgear assembly 100. The forces are counteracted by the selection of the torsional rigidity and bending rigidity characteristics of adjustment mechanism 104, and/or other components of the headgear assembly 100, such as the side arms 102 and the straps 110, 112, 114, the combination of which significantly increases the level of rotational stability for the headgear assembly 100 and interface 10. In some embodiments, the adjustment mechanism 104 is semi-rigid in one or more directions and less rigid in one or more other directions. In some configurations, the adjustment mechanism 104 is configured to be substantially rigid in a width or vertical direction, in use. In some configurations, the adjustment mechanism 104 is configured to be substantially rigid in a lengthwise, longitudinal or horizontal direction, in use. In some configurations, the adjustment mechanism 104 is configured to be less rigid in a third direction, such as a thickness direction or toward and away from the cheeks of the user, in use. This flexibility in one direction allows the adjustment mechanism 104 to conform to a user's head while providing rigidity in a direction that stabilizes and minimizes dislodging of the interface on a user's face.

Figure 7A:
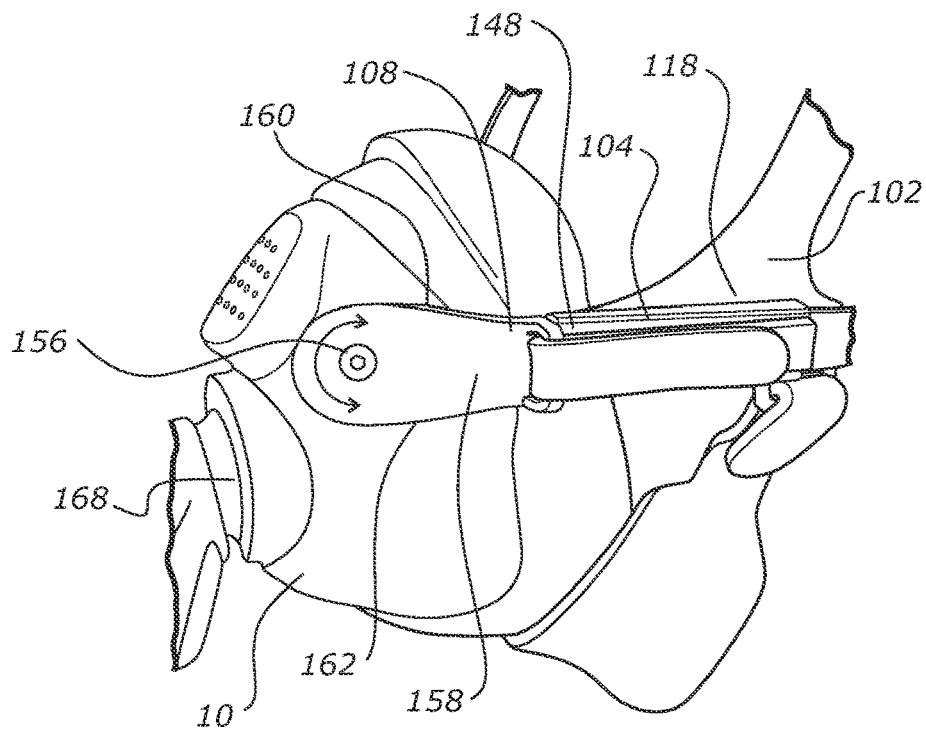
FIG. 7A illustrates a side view of a pivot connection of the headgear assembly and the interface of FIG. 2A.
Figure 7B:
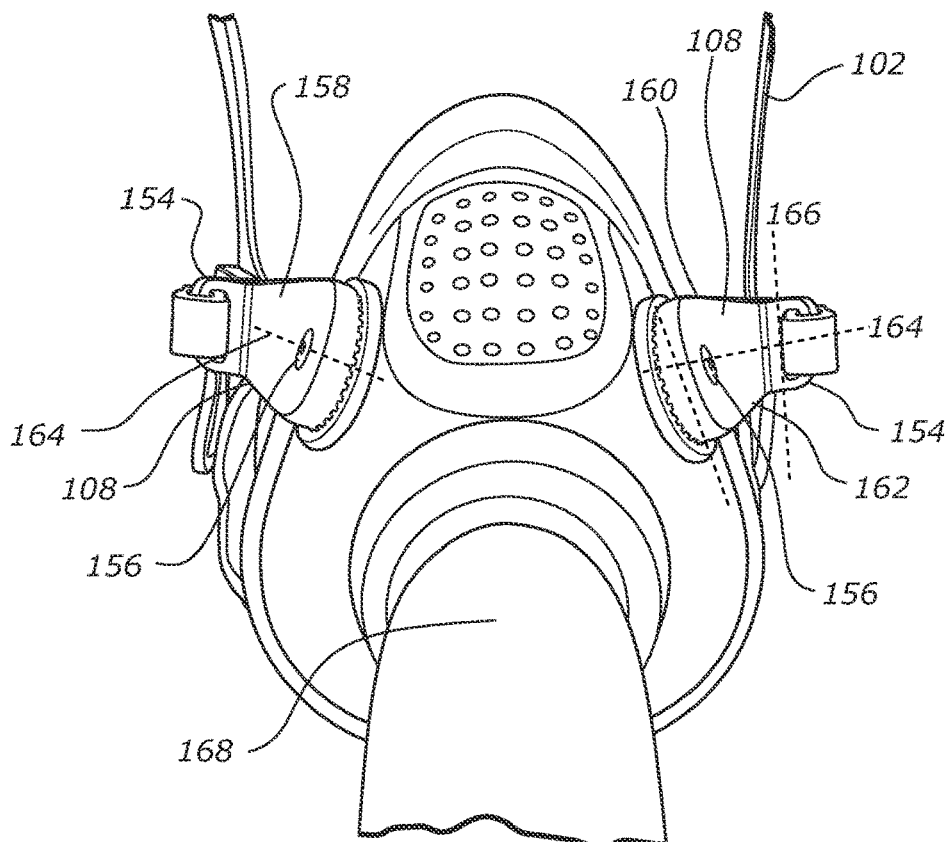
FIG. 7B illustrates a front view of the pivot connection of the headgear assembly and the interface of FIG. 2A.
Figure 7C:
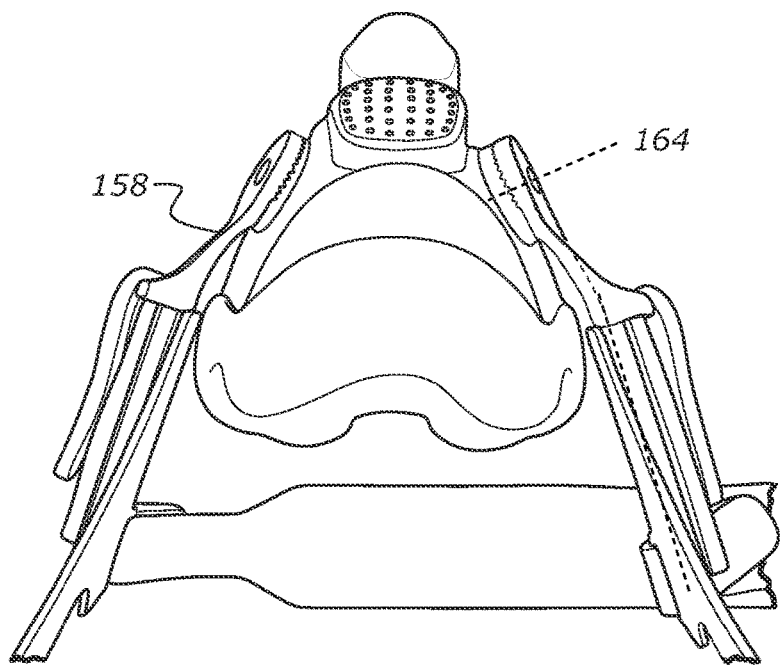
FIG. 7C illustrates a top view of the pivot connection of the headgear assembly and the interface of FIG. 2A.

FIGS. 7A-7C illustrate the pivot connection 156 between the interface 10 and the headgear assembly 100. The interface 10 includes lateral sides. The lateral sides form a generally triangular shape of the interface 10, such that the lateral sides are skewed relative to a vertical plane. As described herein, the connecting member 108 includes the pivot connection 156. The pivot connection provides a pivotal or rotational movement of the connecting member 108, and therefore the headgear assembly 100, relative to the interface 10. The connecting member 108 is designed to lie flat against the lateral sides of the interface 10.

The pivot connection 156 is provided between a front end of the connecting member 108 and the upper lateral sides of the interface 10. The pivot connection 156 includes a pivot axis 164. The pivot connection 156 pivots about a pivot axis 164 and allows the angle of the interface 10 relative to the side arms 102 to be adjusted as per the arrow in FIG. 7A. The pivot axes 164 are centrally located on the lateral sides of the housing of the interface 10, as shown in FIGS. 7B and 7C. The pivot axes 164 are located above the air inlet 168. In some embodiments, the pivot axes 164 are located below the air inlet 168.

The pivot connection 156 has a high level of friction between the connecting member 108 and the interface 10 to allow the angle of the connecting member 108 to be selectively changed by a user but to prevent unintentional angular adjustment when the interface 10 is in use. A high friction washer (e.g., made from an elastomer) is positioned between the pivot connection 156 of the connecting member 108 and the interface 10. Other embodiments to provide friction between the connecting member 108 and the interface 10 are contemplated. In some embodiments, the pivot connection 156 has a low level of friction between the connecting member 108 and the interface 10.

The connecting member 108 can include a transition 158. The transition 158 is located between the pivot connection 156 and the male component 148. The transition 158 includes an upper edge 160 and a lower edge 162. The connecting member 108 includes the transition 158 which twists to change the plane that the male component 148 of the adjustment mechanism 104 lies in. The upper edge 160 is twisted outwards relative to the lower edge 162, so that the male component 148 and pull tab loop 154 lie along a substantially vertical plane. The twist is shown in FIG. 7B which shows the transition between the skewed plane of the pivot connection 156 and the vertical plane of the male component 148 and the pull tab loop 154. The connecting member 108 includes a vertical plane 166 near the pull tab loop 154. The pivot axis 164 is skewed relative to the vertical plane 166. The transition 158 provides a planar connection between the male component 148 and the female component 138 to enable free movement there between. The transition 158 enables the lower ends 118 of the side arms 102 to be aligned with the user's cheeks so that the side arms 102 sit flush against the cheeks and the edges of the side arms 102 do not dig in.

Figure 8:
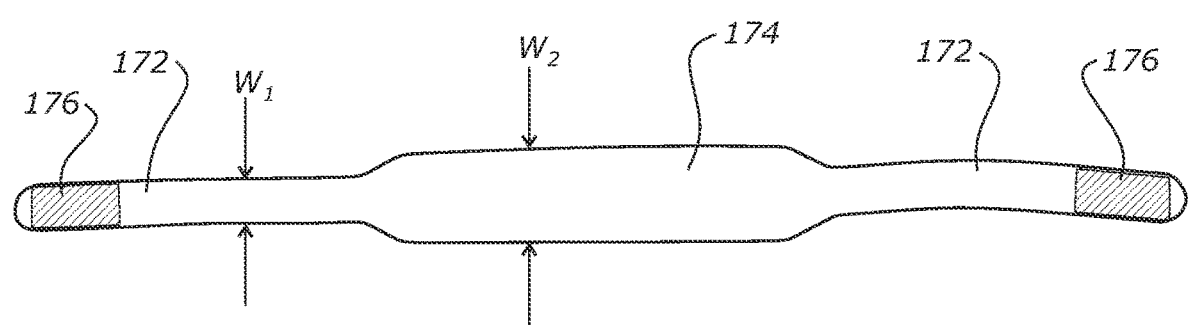
FIG. 8 illustrates a chin strap of the headgear assembly of FIG. 2A.

FIG. 8 illustrates an embodiment of a strap which includes two lateral ends 172 and a middle portion 174 there between. The chin strap 110, the top strap 112, and the rear strap 114 can have any or all of the following features of the strap shown in FIG. 8.

The lateral end 172 is sized to be passed through the aperture of the corresponding strap connection point of the side arm 102. The lateral ends 172 have a width $W_1$ that is narrower than a width $W_2$ of the middle portion 174. The narrower lateral ends 172 are configured to pass through apertures in the side arms 102 and double back on themselves. The wider middle portion 174 acts as an end stop to prevent over tightening of the strap. The middle portion 174 is sized not to pass through the apertures in the side arms 102. The middle portion 174 can be enlarged to provide increased stability and comfort on the user's head. Each lateral end 172 can include a fastener 176. The fastener 176 can be a component (e.g., hook component) of a hook and loop fastener such that the fastener 176 is configured to pass through and around the corresponding aperture on the side arm 102. The fastener 176 can be secured to another part of the strap, which acts as the other component, to secure the headgear assembly 100 in a configuration that fits the user's head. The fastener 176 can be secured after the headgear assembly 100 is positioned to provide an effective seal between the user's face and the interface 10.

The chin strap 110, the top strap 112, and the rear strap 114 are made from any suitable material. The chin strap 110, the top strap 112, and/or the rear strap 114 are made from foam and textile laminate material (e.g. Breathoprene™). The top strap 112 is inelastic. In some embodiments, the top strap 112 is elastic. The chin strap 110 is elastic. In some embodiments, the chin strap 110 is inelastic. The rear strap 114 is elastic. In some embodiments, the rear strap 114 is inelastic. Other combinations of elastic and inelastic straps are contemplated.

FIGS. 1-8 illustrate various embodiments of components of headgear assembly 100. The features of any embodiment described herein can be combined with any other embodiment described herein. Any of the following features can be included separately or in combination with components described herein. The adjustment mechanism 104 is integrally formed with the side arm 102. In some embodiments, the adjustment mechanism 104 is not integrally formed with the side arm 102. The female component 138 can be integrally formed with the support 132 of the side arm 102.

Figure 11:
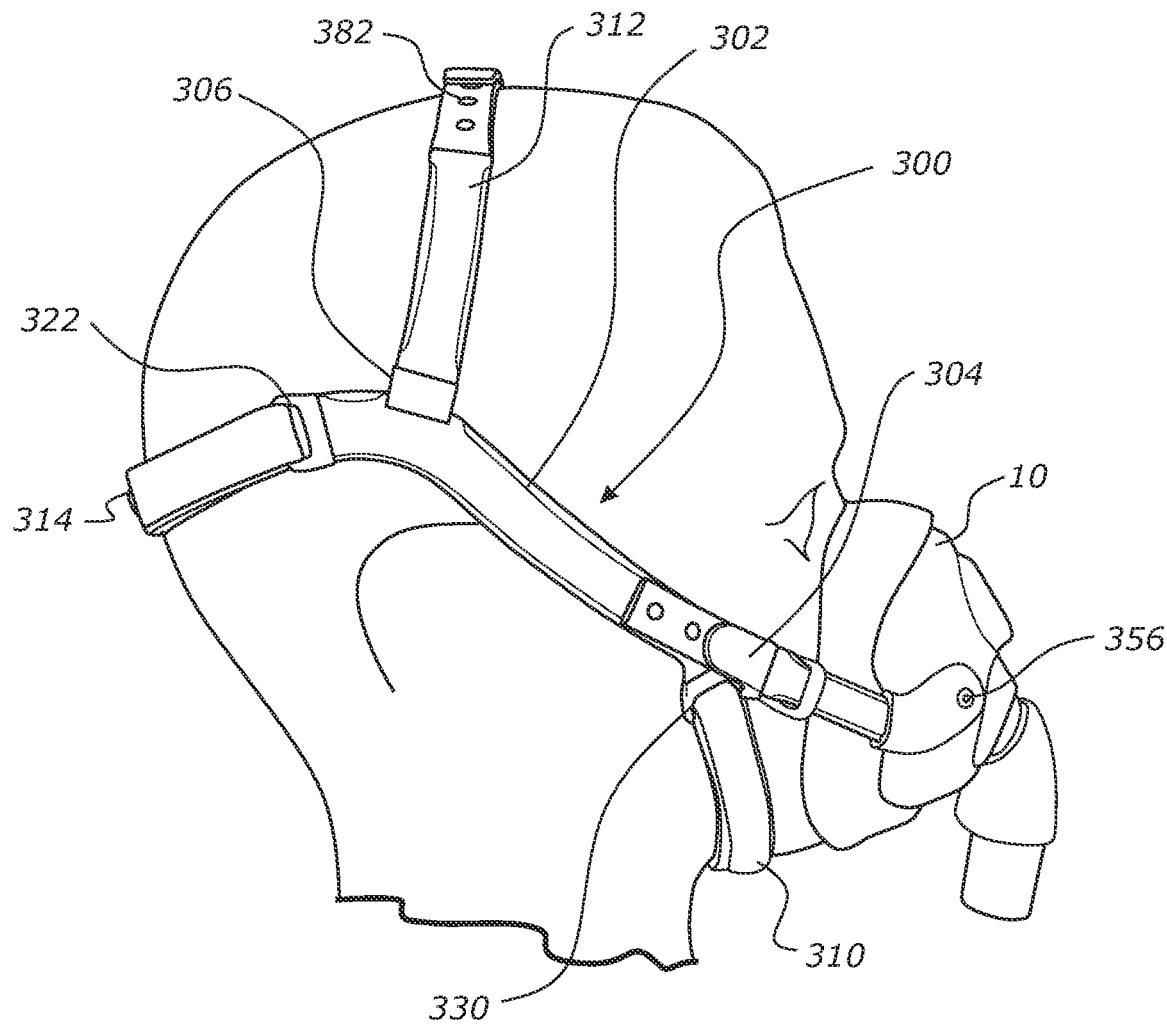
FIG. 11 illustrates a side view of a user, a headgear assembly, and an interface.
Figure 12:
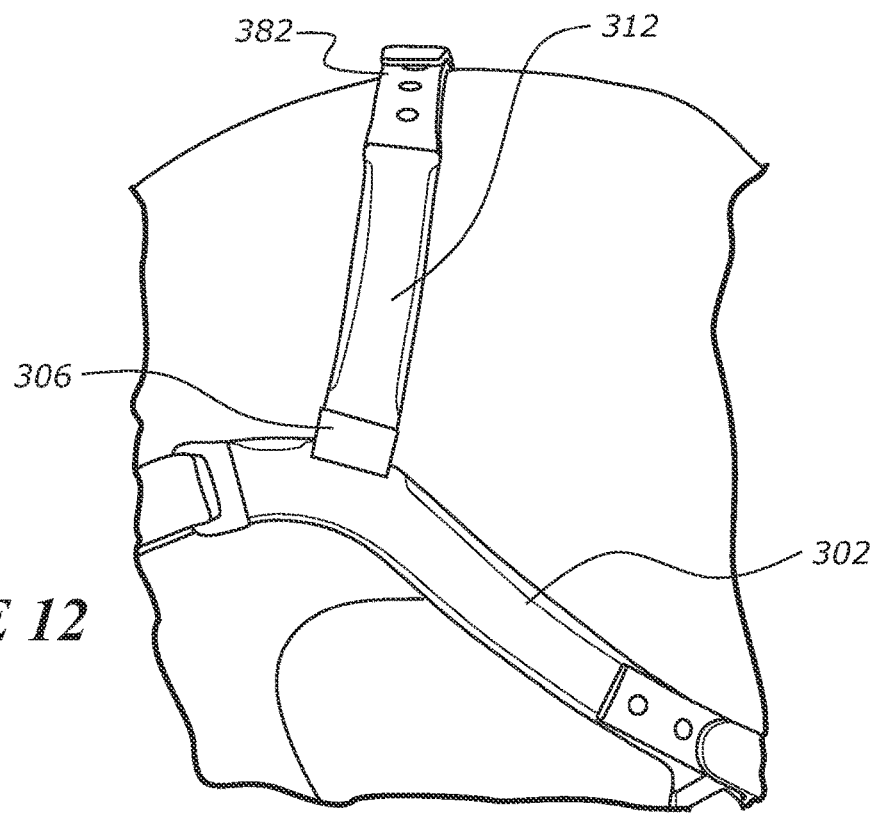
FIG. 12 illustrates a side view of the user and the headgear assembly of FIG. 11.
Figure 13:
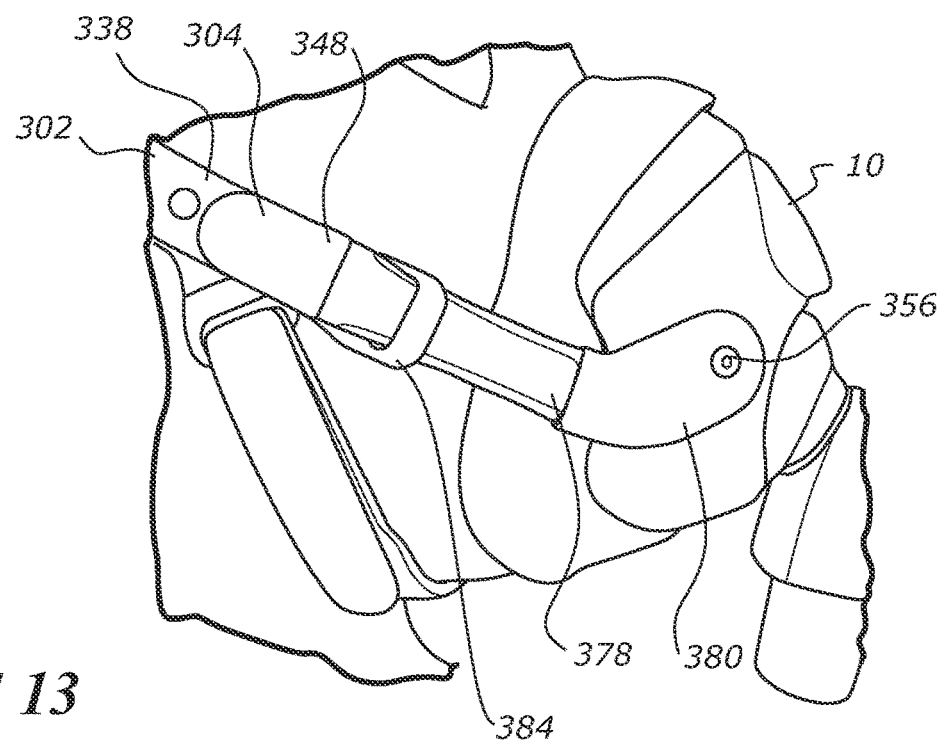
FIG. 13 illustrates a side view of an adjustment mechanism of the headgear assembly and the interface of FIG. 11.

Each of the side arms 102 is intra-moulded as described herein. In some embodiments, the side arms 102 are not intra-moulded. FIGS. 11-13 provide examples of intra-moulded side arms. The side arm 102 includes a textile casing that completely surrounds a core. The textile casing is a tube or other enclosed shaped. The core comprises a plastic material which provides strength to the textile casing. As described herein, one or more additional components can be formed by the same process, such as the top strap, the rear strap and/or the chin strap. In some intra-moulding processes, a molten plastic is injected onto a textile material or into a preformed textile casing. The intra-moulded side arm 102 includes a cover layer partially or completely surrounding a core. The cover layer can be constructed from a soft fabric, textile, foam or similar cushioning materials on at least an internal surface of the side arm 102. The core may be formed by injection moulding a semi-rigid plastic into a cavity or hollow center of the cover layer. The intra-moulded side arms 102 include a textile or foam covering on at least an internal surface.

Other or alternative configurations are contemplated. In some embodiments, the adjustment mechanism 104 is omitted. In some embodiments, the side arms 102 could be permanently and/or rigidly connected to the interface 10. In some embodiments, the components have different shapes. In some embodiments, the connecting member 108 can extend further laterally from the sides of the interface 10. This arrangement would reduce contact between the side arms 102 and the user's cheeks which may improve comfort.

In some embodiments, the adjustment mechanism 104 is in the reverse arrangement than the configuration shown in FIGS. 1-8. The side arm 102 includes the male component 148. The connecting member 108 includes the female component 138. The male component 148 couples or is formed with the support 132 of the side arm 102. The support arm 102 and/or the male component 148 include the pull tab loop 154. The side arms 102 can form the male component 148 and/or the pull tab loop 154. The female component 138 couples or is formed with the connecting member 108. The pull tab 140 couples to the female component 138. In this configuration, the user pulls the pull tab 140 toward the interface 10 to adjust to adjust the distance of the adjustment mechanism 104.

The adjustment mechanism 104 allows for continuous sliding or telescoping positions, as per the embodiment of FIGS. 1-8. In some embodiments, the adjustment mechanism 104 allows for discrete adjustment. In some embodiments, the adjustment mechanism 104 includes a ratchet for incremental adjustment. The male component 148 can include gears or teeth. The female component 138 can include a pawl. The distance that the adjustment mechanism 104 can travel is determined by the size of the gears or teeth.

The straps can include any configuration or shape. One or more straps are adjustable by the user by adjusting the fasteners 176 connected to the lateral ends 172. In some embodiments, the rear strap 114 is not adjustable. The rear strap 114 has a fixed length. In some embodiments, the top strap 112 is not adjustable. The top strap 112 has a fixed length. The chin strap 110, top strap 112, and the rear strap 114 can be any combination of elastic or inelastic. The chin strap 110 can be elastic or inelastic. The top strap 112 can be elastic or inelastic. The rear strap 112 can be elastic or inelastic. Two or more straps can be elastic. Two or more straps can be inelastic. The top strap 112 can have a fit and forget arrangement. In the fit and forget arrangement, the top strap 112 is adjusted once by the user to fit around the crown of the head. In subsequent uses, the user does not have to remove or adjust the top strap 112. The rear strap 114 can have a fit and forget arrangement. In some embodiment, rear strap 114 is adjusted once by the user to fit around the back of the head. In subsequent uses, the user does not have to remove or adjust the rear strap 114. Instead the user can apply the headgear assembly 100 using a similar method as a baseball cap by placing the top strap 112 and/or the rear strap 114 against the head and bringing the interface 10 toward the face. Examples of fit and forget arrangements are included in FIGS. 11 and 12. The top strap 112 is intra-moulded as described herein. The rear strap 114 is intra-moulded as described herein. In some embodiments, the top strap 112 is integrally formed with the side arms 102. In some embodiments, the rear strap 114 is integrally formed with the side arms 102.

The pivot connection 156 can have any configuration or shape. In some embodiments, the pivot connection 156 has discrete positions. In some embodiments, the pivot connection 156 allows for infinite rotational positions. In some embodiments, the pivot connection 156 includes a ratchet style adjustment. In some embodiments, the pivot connection 156 is low friction to allow the interface 10 to self-adjust to various angles on the user's face. In some embodiments, the pivot connection 156 is high friction to maintain the position of the pivot connection 156. In some embodiments, the pivot connection 156 is provided by a malleable metal joint.

The headgear assembly 100 is used in conjunction with an interface that seals around the nose and mouth. In some embodiments, the headgear assembly 100 is used in conjunction with an interface that seals around the nose. In some embodiments, the headgear assembly 100 is used in conjunction with an interface that seals around the mouth. In some embodiments, the headgear assembly 100 is used in conjunction with an interface that seals under the nose.

Figure 9:
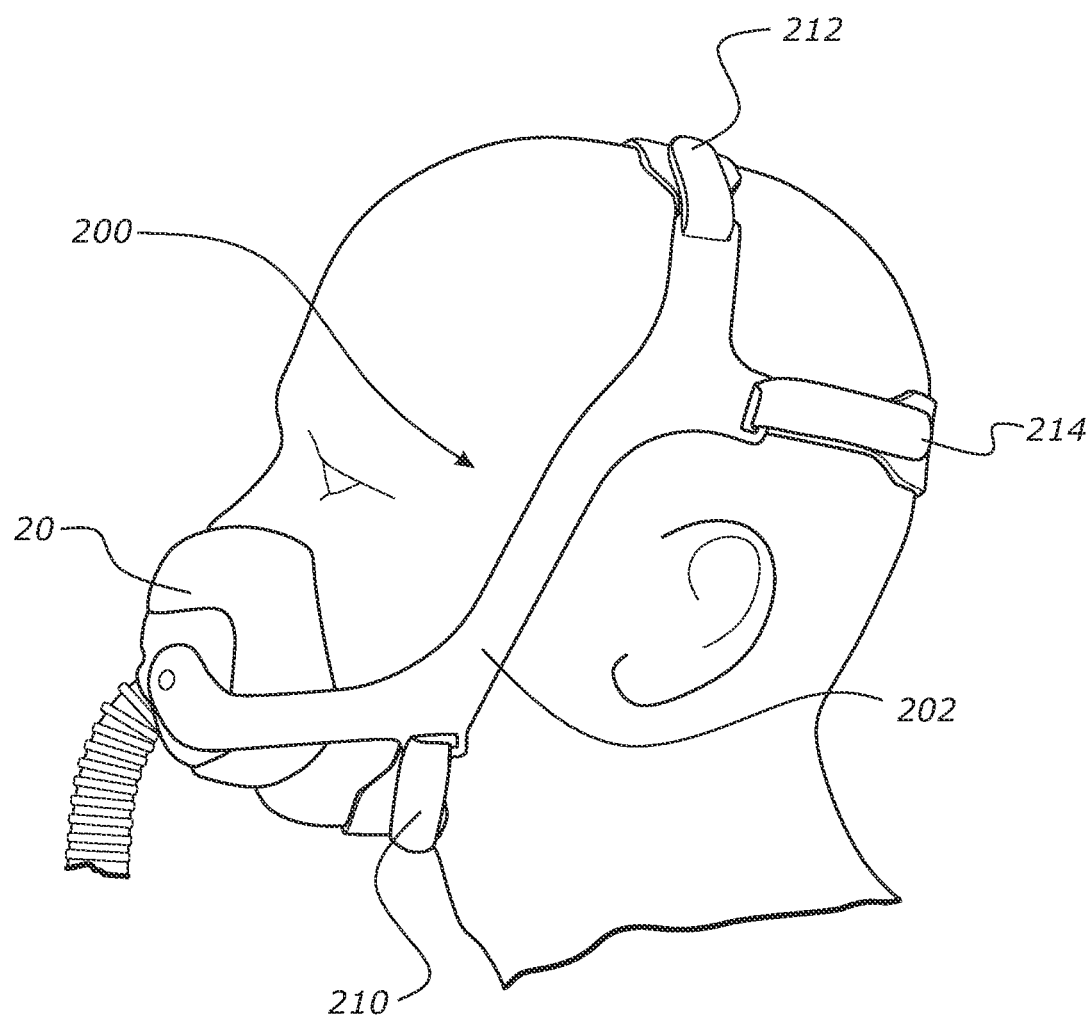
FIG. 9 illustrates a side view of a user, a headgear assembly, and an interface.

FIG. 9 illustrates an interface 20 and a headgear assembly 200 including semi-rigid side arms 202, as described herein. The headgear assembly 200 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 200 can include any features of the headgear assemblies described herein. The headgear assembly 200 can include a chin strap 210, a top strap 212, and a rear strap 214.

Figure 10A:
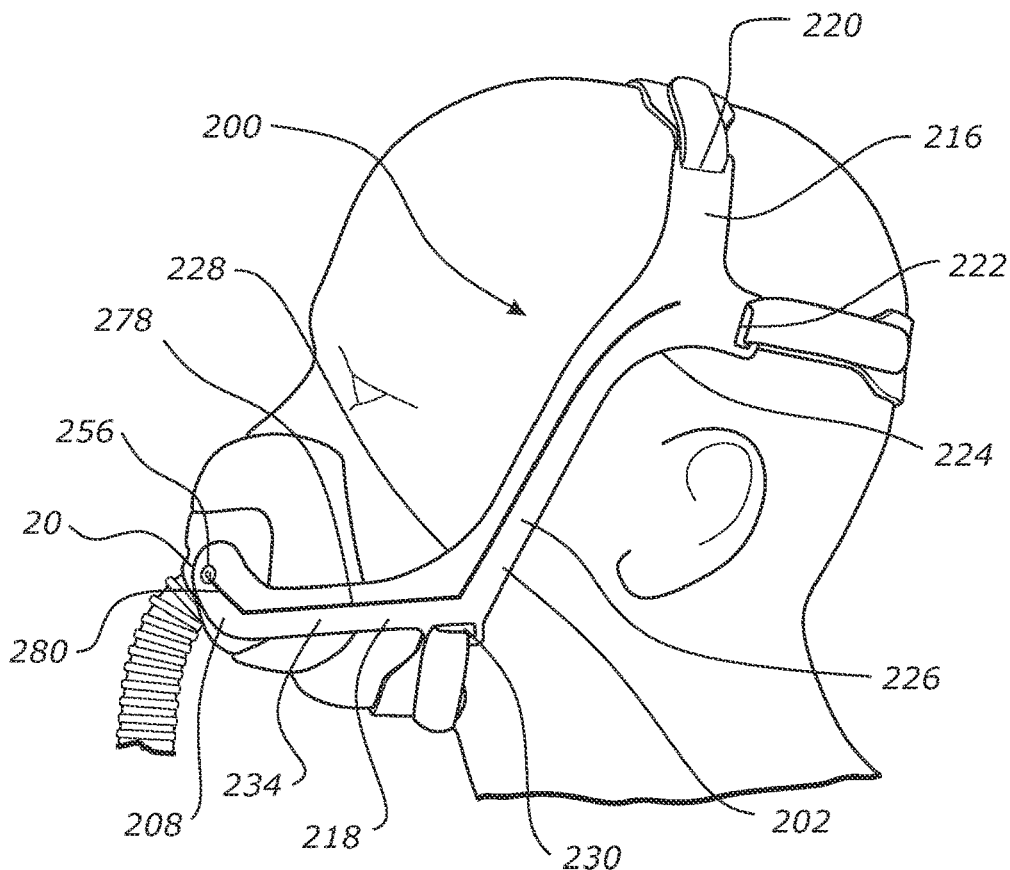
FIG. 10A illustrates a side view of the user, the headgear assembly, and the interface of FIG. 9.
Figure 10B:
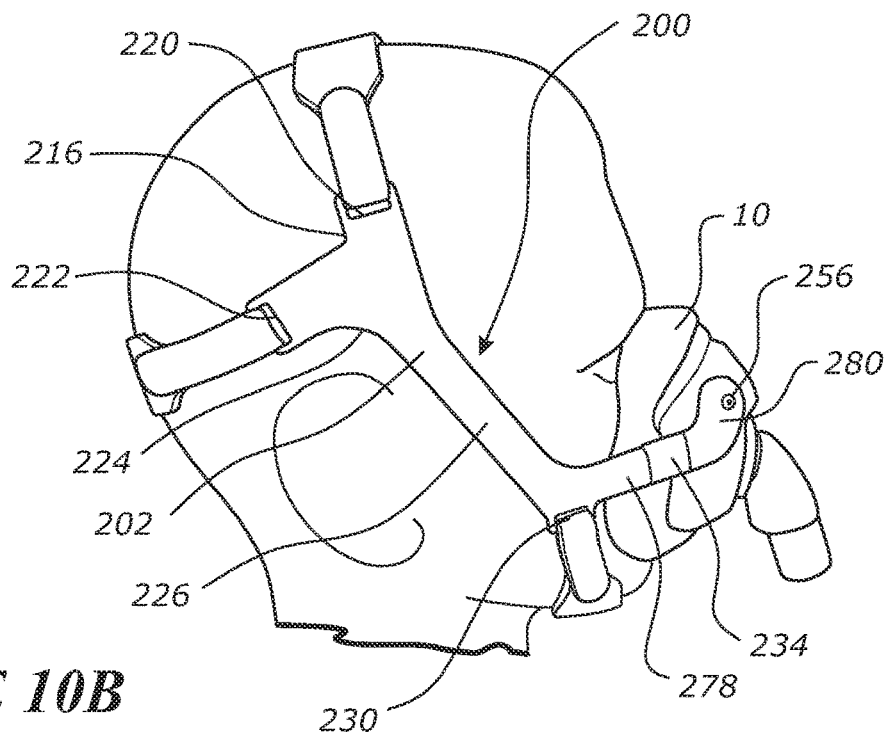
FIG. 10B illustrates a side view of the user and the headgear assembly of FIG. 9 and an interface.

The headgear assembly 200 can be used with any interface including those described herein. FIG. 10A illustrates a side view of the headgear assembly 200 of FIG. 9. The headgear assembly 200 is used in combination with an interface 20 that seals around a user's mouth and on the lower surfaces of the user's nose. The interface 20 can seal on the lateral lower sides or flanks of the user's nose. The seal exposes the tip of the user's nose. The interface 20 does not seal on the bridge of the user's nose. FIG. 10B illustrates a side view of the headgear assembly 200. The headgear assembly 200 is used in combination with the interface 10 which is an over-the-nose full-face interface that is configured to seal on or near the bridge of the user's nose.

The headgear assembly 200 can include a pair of opposing semi-rigid side arms 202. Each side arm 202 is designed to be positioned on one side of head of the user. While only one side arm 202 is shown in FIG. 10A, the other side arm 202 can have the same or similar features and can be a mirror image of the illustrated side arm 202. The headgear assembly 200 can include a connecting member 208 that connects the side arms 202 to the interface 20.

The side arm 202 includes an upper end 216 and a lower end 218. The upper end 216 is bifurcated and forms a top strap connection point 220 and a rear strap connection point 222. The side arm 202 includes an ear arch 224. The ear arch 224 passes above the ear of the user in use. The side arm 202 includes a mid-section 226 between the upper end 216 and the lower end 218. The side arm 102 includes a cheek curve 228. The cheek curve 228 passes near the cheekbone of the user in use.

The lower end 218 is bifurcated and forms a chin strap connection point 230 and an extension 234. The extension 234 extends toward or to the interface 20. The extension 234 includes a pivot connection 256. The lower ends of the side arms 202 are permanently coupled to the interface 20 via the pivot connection 256. The lower ends of the side arms 202 are not intended for consumer removal from the interface 20. The lower ends of the side arms 202 form a pivot connection 256 with the interface 20. The headgear assembly 200 does not include an adjustment mechanism as described in FIGS. 2A-8.

The extension 234 of the side arms 202 includes two segments 278, 280. The two segments 278, 280 form an elbow, bend, or dog-leg. The segment 278 is horizontal or substantially horizontal in use. The segment 280 bends or extends upwards towards the pivot connection 256 from the segment 278. This two segment construction allows a force vector to be applied to the interface 20 closer to the chin region. This two segment construction counteracts blow-off forces and minimizes leaks in this area. The construction also allows the interface 20 to pivot at a location close to the center of the interface 20 which allows the amount of engagement between the interface 20 and the user's nose to be adjustable. The interface 10 can be pivoted such that the upper half of the interface 10 is rotated towards the user's nose thus increasing engagement with the nose. The interface 10 can be pivoted such that the upper half of the interface 10 is rotated away from the nose. The interface 10 can be pivoted until the preferred fit is achieved.

FIG. 11 illustrates an interface 10 and a headgear assembly 300 including integrally formed side arms 302 and a top strap 312. The headgear assembly 300 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 300 can include any features of the headgear assemblies described herein. While only one side arm 302 is shown in FIGS. 11-13, the other side arm 302 can have the same or similar features and can be the same or similar to of the illustrated side arm 302. As described herein, the side arms 302 are integrally formed with the top strap 312. The male and female components of the top strap 312 are connected to the respective side arm 302. In the illustrated embodiment, the side arm 302 on the user's right side is connected to the female component of the top strap 312 and the side arm 302 on the user's left side is connected to the male component of the top strap 312, but the reverse configuration is contemplated. The headgear assembly 300 can include the chin strap 310 and the rear strap 314. The side arm 302 includes a rear strap connection point 322. The side arm 302 includes a chin strap connection point 330. The headgear assembly includes the adjustment mechanism 304 and the pivot connection 356. The rear strap 314 is adjustable. In some embodiments, the rear strap 314 is not adjustable. The chin strap 310 is adjustable. In some embodiments, the chin strap 310 is not adjustable. The chin strap 310 has a single width over the length of the chin strap 310. In some embodiments, the chin strap 310 has two or more widths over the length of the chin strap 310. FIG. 12 shows the upper end of the headgear assembly 300 and FIG. 13 shows the lower end of the headgear assembly 300.

The headgear assembly 300 includes the integrally formed side arms 302 and top strap 312. The side arms 320 and the top strap 312 are integrally formed as a single component. The side arms 302 and/or the top strap 312 can include a textile covering. The textile covering covers at least a portion of the side arms 302 and/or the top strap 312. In some embodiments, the textile covering covers the side arms 302 and/or the top strap 312 in their entirety. The side arms 302 and/or the top strap 312 are intra-moulded. In some methods of manufacturing of the side arms 302, molten plastic is injected into one or more textile tubes. The plastic and the textile tubes form a unitary structure. The side arms 302 and the top strap 312 can be separately formed and later joined at a connector 306. The connector is formed during an over-molding process, but could be formed during the intra-moulding process.

The top strap 312 includes an adjustment mechanism 382 that allows for incremental adjustment of the top strap 312. The adjustment mechanism 382 is located at a central location. The top strap 312 can include two portions or halves that are adjustably connected. The adjustment mechanism 382 includes a male component and a female component that are adjusted to form the top strap 312. The adjustment mechanism 382 can be incrementally and discretely adjusted. The headgear assembly 300 can include a baseball cap style adjustment arrangement including a button or post on one half or portion of the top strap that is received by any one of several spaced apart holes on the opposing half or portion of the top strap. The post can form a snap-fit or interference fit with the hole such that the adjustment mechanism 382, and therefore the top strap 312, is secure. Other types of fasteners are contemplated to provide the adjustment of the top strap 312. The adjustment mechanism 382 is considered a fit and forget configuration in which the headgear assembly 300 is adjusted once and there may be no need to adjust on a regular basis. The adjustment mechanism 382 is integrally formed with top strap.

Referring to FIG. 13, the side arms 302 includes two segments 378, 380. The two segments 378, 380 form an elbow, bend, or dog-leg. The segment 378 extends across the user's cheek in use. The side arms 302 are straighter across the user's cheeks than with headgear assembly 100. The segment 380 bends upwards towards the pivot connection 356. This two segment construction allows a force vector to be applied to the interface 10 closer to the chin region. This two segment construction counteracts blow-off forces and minimizes leaks in this area. The construction also allows the interface 10 to pivot at a location close to the center of the interface 10 which allows the amount of engagement between the interface 10 and the user's nose to be adjustable.

The adjustment mechanism 304 allows for incremental adjustment of the position of the interface 10 relative to the headgear assembly 300. The adjustment mechanism 304 includes a female component 338 that is integrally formed at a forward and lower end of the side arms 302. The adjustment mechanism 304 includes a male component 348 that is connected to the interface 10 by the pivot connection 356.

The female component 338 includes a guide loop 384 at its forward end. The guide loop 384 is configured to receive the male component 348 and guide the male component 348 into alignment with the female component 338. The guide loop 384 also prevents rotation of the male component 348 relative to the female component 338 so that forces can be effectively transferred from the interface 10 to the headgear assembly 300. The guide loop 384 limits or prevents the male component 348 from being completely disconnected from the female component 338. The guide loop 384 provides friction to maintain or catch the male component 348 relative to the female component 338. The guide loop 384 limits or prevents disassembly of the adjustment mechanism 304. However, other suitable types of anti-rotate arrangements could also be used.

The adjustment mechanism 304 allows for incremental adjustment between the side arms 202 and the interface 10. The male component 348 includes a button or post that is configured to be received in one of a plurality of apertures in the female component 338 to provide a baseball cap style adjustment arrangement. The post can form a snap-fit or interference fit with the aperture or hole such that the adjustment mechanism 304, and therefore the side arm 202, is secured in an adjusted position. The adjustment mechanism 304 includes multiple buttons or posts. The adjustment mechanism 304 includes a hook and loop fastener. Other configurations of fasteners are contemplated for the male component 348 and the female component 338. The adjustment mechanism 304 can be incrementally and discretely adjusted. The adjustment mechanism 304 is considered a fit and forget configuration in which the headgear assembly 300 is adjusted once and there may be no need to adjust on a regular basis. Once the adjustment mechanisms 304, 382 are fitted to the user, the user pulls on the headgear assembly 300 like baseball cap. The user places the interface 10 in position and slides the top strap 312 around the crown of the head. Alternatively, the user places top strap 312 around the crown of the head and slides the interface 10 in position.

Figure 14A:
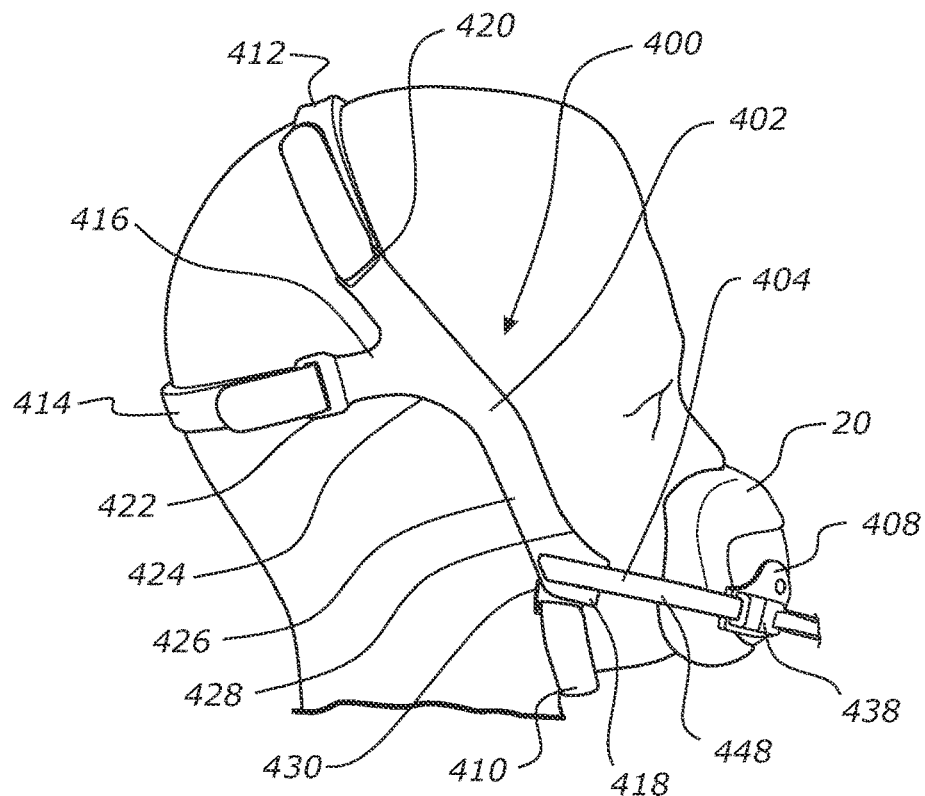
FIG. 14A illustrates a side view of a user, a headgear assembly, and a full-face under-nose interface.
Figure 14B:
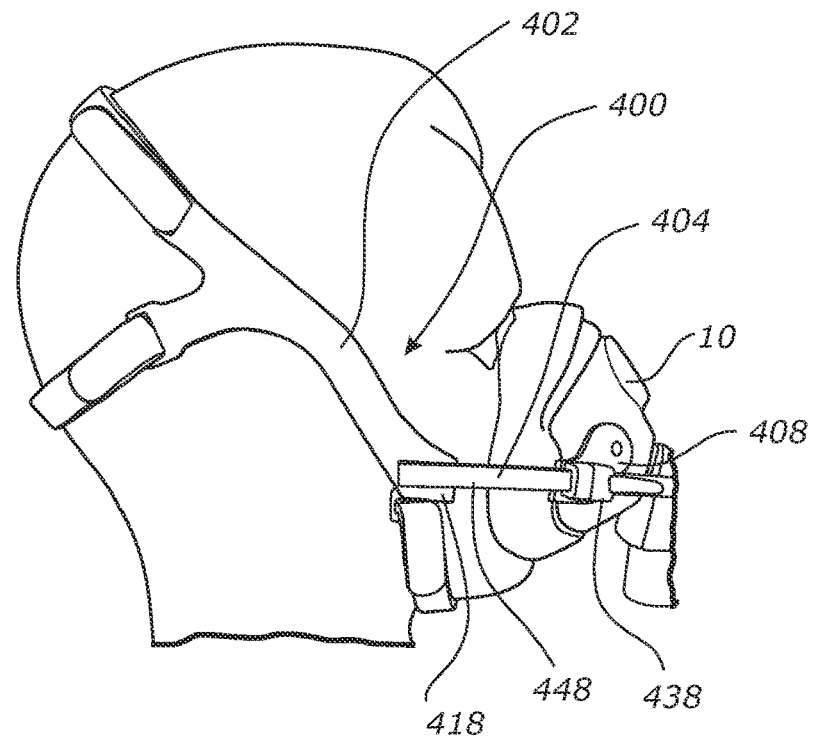
FIG. 14B illustrates a side view of the user, the headgear assembly of FIG. 14A, and a full-face over-nose interface.
Figure 15:
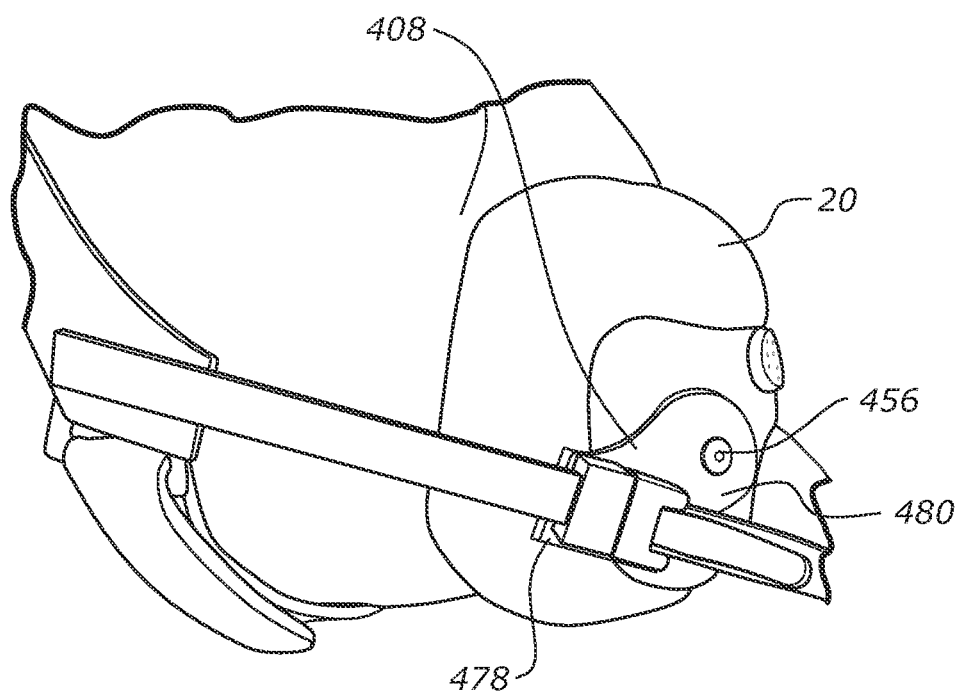
FIG. 15 illustrates a side view of an adjustment mechanism of the headgear assembly and the interface of FIG. 14A.

FIG. 14A illustrates the interface 20 and a headgear assembly 400 including a ratchet style adjustment mechanism 404. The headgear assembly 400 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 400 can include any features of the headgear assemblies described herein. While only one side arm 402 is shown in FIGS. 14A-15, the other side arm 402 can have the same or similar features and can be a mirror image of the illustrated side arm 402.

The headgear assembly 400 includes a chin strap 410, a top strap 412, and a rear strap 414. The headgear assembly 400 includes the side arm 402. The chin strap 410 has a constant width. The top strap 412 has a constant width. The rear strap 414 has a constant width. In some embodiments, the chin strap 410 does not have a constant width. In some embodiments, the top strap 412 does not have a constant width. In some embodiments, the rear strap 414 does not have a constant width.

The side arm 402 includes an upper end 416 and a lower end 418. The upper end 416 is bifurcated into a top strap connection point 420 and a rear strap connection point 422. The side arm 402 includes an ear arch 424. The ear arch 424 passes above the ear of the user in use. The side arm 402 includes a mid-section 426 between the upper end 416 and the lower end 418. The side arm 102 includes a cheek curve 428. The cheek curve 428 passes near the cheekbone of the user in use. The lower end 418 includes a chin strap connection point 430. The lower end 418 couples to the adjustment mechanism 404.

The adjustment mechanism 404 comprises a ratchet or cable tie type mechanism. The adjustment mechanism 404 provides incremental adjustment of the length between the side arms 402 and a connecting member 408. The adjustment mechanism 404 provides incremental adjustment of the position of the interface 10, 20 relative to the headgear assembly 400. The adjustment mechanism 404 includes male component 448. The male component 448 couples to or extends from the lower end 418 of the side arm 402. The male component 448 includes a plurality of teeth. The male component 448 can be integrally formed with the side arms 402 by means such as intra-moulding, as described herein.

The adjustment mechanism 404 includes female component 438. The female component 438 couples to the connecting member 408. The female component 438 includes a pawl inside a housing that engages one or more of the teeth of the male component. In other arrangements, the female component could include a cam lock member that provides infinite adjustability. In some embodiments, the arrangement of the adjustment mechanism 404 is reversed. The male component 448 is formed in or with the connecting member 408. The female component 438 is formed in or with the side arms 402.

For the full-face under-nose interface 20, the male component 448 is angled downwards away from the user's face, in use, as shown in FIG. 14A. The male component 448 is angled in a forward direction in comparison to the full-face over-nose interface 10 of FIG. 14B. For the full-face over-nose interface 10, the male component 448 is more horizontal. The lower ends 418 of the side arms 402 are close to horizontal. In some methods of use, variation will occur for differing cranial and/or facial geometries. In some methods of use, variation will occur for different interfaces. The configuration of the adjustment mechanism 404, including the male component 448, allows the headgear assembly 400 to apply a force to the interface 10, 20 in order to counteract blow-off forces. The downwardly angled male component 448 of FIGS. 14A and 15 allow the headgear assembly 400 to apply an upwardly direction force to the interface 20 in order to increase engagement between the interface 20 and the under-side of the user's nose and improve the seal.

Referring to FIG. 15, the connecting member 408 includes two segments 478, 480. The two segments 478, 480 form an elbow, bend, or dog-leg. The segment 480 bends upwards towards the pivot connection 456. This two segment construction allows a force vector to be applied to the interface 20 at chin height, counteracts blow-off forces, minimizes leaks in this area, and allows the interface 20 to pivot at a location close to the center of the interface 20. The two segments 478, 480 direct headgear forces back up towards the centrally located pivot connection 256.

Figure 16A:
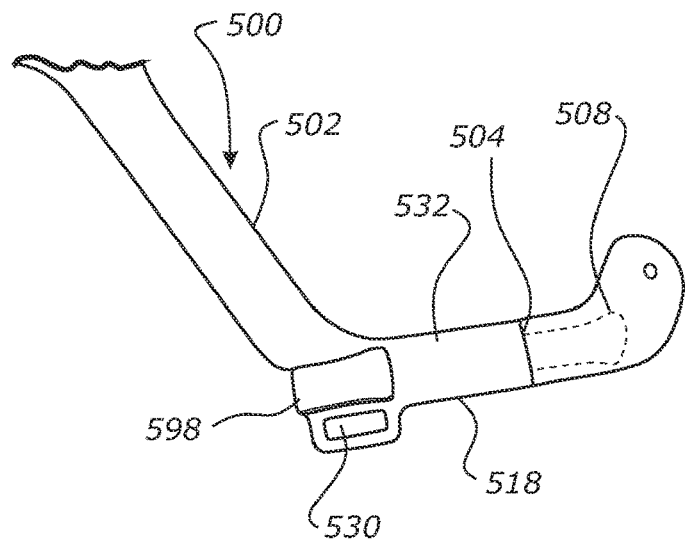
FIG. 16A illustrates a front side view of an adjustment mechanism of the headgear assembly of FIG. 14A.
Figure 16B:
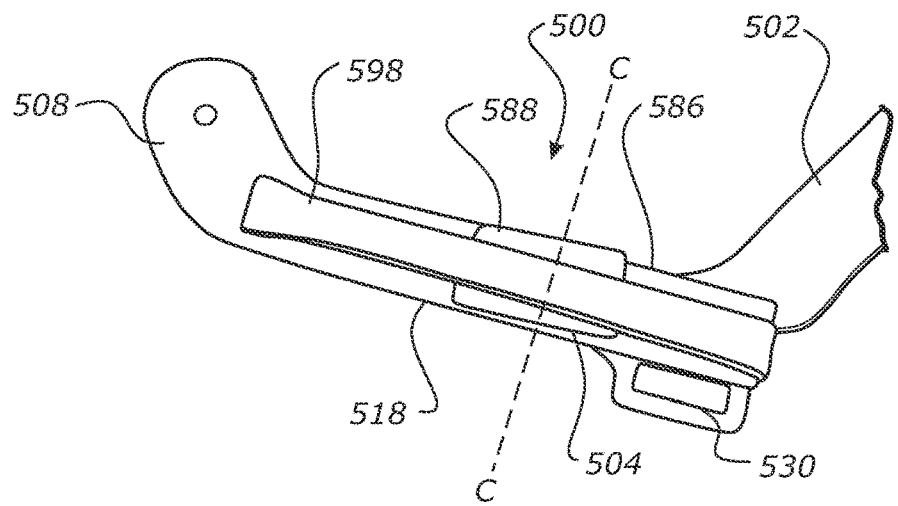
FIG. 16B illustrates a back side view of the adjustment mechanism of the headgear assembly of FIG. 14A.

FIGS. 16A-16B illustrates a headgear assembly 500 including a rail adjustment mechanism 504. The headgear assembly 500 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 500 can include any features of the headgear assemblies described herein. While only one side arm 502 is shown in FIGS. 16A-16B, the other side arm 502 of the headgear assembly 500 can have the same or similar features and can be a mirror image of the illustrated side arm 502. The headgear assembly 500 can include any straps described herein. FIG. 16A is a front side view of the side arm 502. FIG. 16B is a back side view of the side arm 502. The side arm 502 includes a lower end 518. The lower end 518 includes a chin strap connection point 530 and a support 532. The headgear assembly 500 includes the connecting member 508.

Figure 16C:
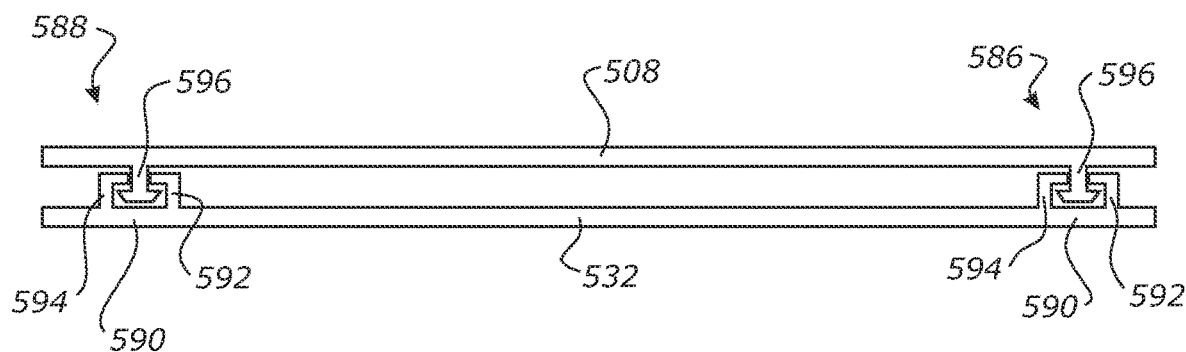
FIG. 16C illustrates a cross-sectional view of the adjustment mechanism of the headgear assembly of FIG. 14A along line C-C in FIG. 16B.

The adjustment mechanism 504 is another embodiment of an adjustment mechanism that can replace the adjustment mechanism 104 of headgear assembly 100 and any adjustment mechanism described herein. The adjustment mechanism 504 comprises two sets of interlocking rails 586, 588 that connect the lower forward end of the side arms 502 and the connecting member 508. FIG. 16C is the cross-sectional view of the two sets of interlocking rails 586, 588 along line C-C in FIG. 16B. The first set of interlocking rails 586 is along the upper edge of the connecting member 508 and the second set of interlocking rails 588 is along the lower edge of the connecting member.

The support 532 has a pair of tracks 590 that protrude from an internal surface of the support 532. Each of the tracks 590 comprises a pair of opposing rails 592, 594 that form an elongate channel or female component of the adjustment mechanism 504. The connecting member 508 has a pair of single rails 596 that protrude from an internal surface of connecting member 508. The single rails 596 are spaced apart, with one on each elongate edge of the connecting member 508. Each of the single rails 596 is received and retained in the channel of one of the tracks 590. The reverse configuration of the support 532 and the connecting member 508 is contemplated. The second set of interlocking rails 588 along the lower edge can have the same configuration or a different configuration as the first set of interlocking rails 586 along the upper edge.

The two sets of interlocking rails 586, 588 can include one or more features to retain or interlock the tracks 590 and the single rails 596. The tracks 590 have a flange that engages with a corresponding flange of the single rail 596 to retain the single rail 596 within the channel of the tracks 590. Each opposing rail 592, 594 has a flange and the corresponding single rail 596 has two flanges. In some embodiments, at least one opposing rail 592, 594 has a flange and the corresponding single rail 596 has at least one flange. The two sets of interlocking rails 586, 588 are designed to permit sliding there between but limit disengagement. The two sets of interlocking rails 586, 588 are disposed horizontally in use. The two sets of interlocking rails 586, 588 include a male component designed to be received in and inlock with a female component. The tracks 590 function as the female component and the single rail 596 functions as the male component of the adjustment mechanism 504. In some embodiments, one set of interlocking rails is utilized. The two sets of interlocking rails 586, 588 allow the connecting member 508 to slide relative to the side arm 502. Other configurations are contemplated for creating a sliding connection.

Referring back to FIGS. 16A and 16B, the headgear assembly 500 includes a biasing elastic 598. The biasing elastic 598 couples to a forward end of the connecting member 508 and a rear end of the side arms 502. The biasing elastic 598 can have any connection point between the connecting member 508 and the side arms 502. The biasing elastic 598 is configured to bias the adjustment mechanism 504 towards an un-extended or neutral position as shown in FIG. 16A. FIG. 16B illustrates the biasing member 598 extending beyond the neutral position. The biasing elastic 598 has a longer length in FIG. 16B than in FIG. 16A. The biasing elastic 598 extends as the interlocking rail 588 coupled to the connecting member 508 slides along the interlocking rail 586 coupled to the side arm 502 in a direction that increases a length of the adjustment mechanism 504. The biasing elastic 598 has the effect of pulling the interface 10, 20 towards the user's face to increase the sealing force. In some arrangements, the biasing elastic 598 may have relatively flat force extension profile so that the sealing force applied by the biasing elastic 598 is not overly large when the user's head is larger. In some arrangements, the biasing elastic 598 could be omitted and a retention mechanism could be employed to secure the adjustment mechanism 504 in an adjusted position.

Figure 17A:
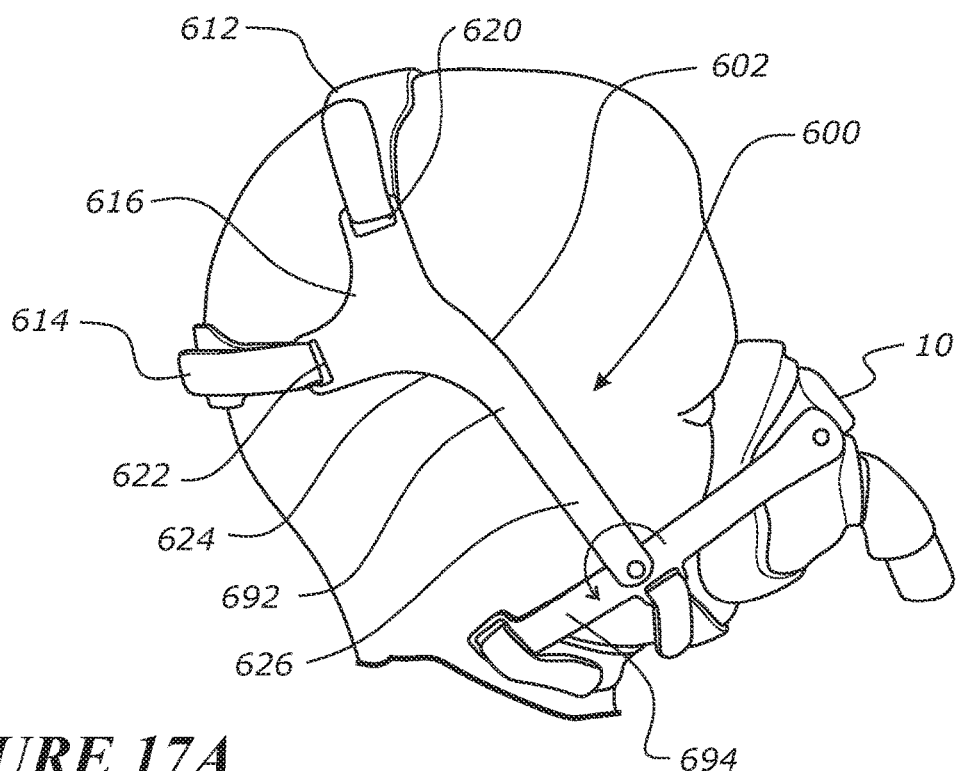
FIG. 17A illustrates a side view of a user, a headgear assembly, and an interface.
Figure 17B:
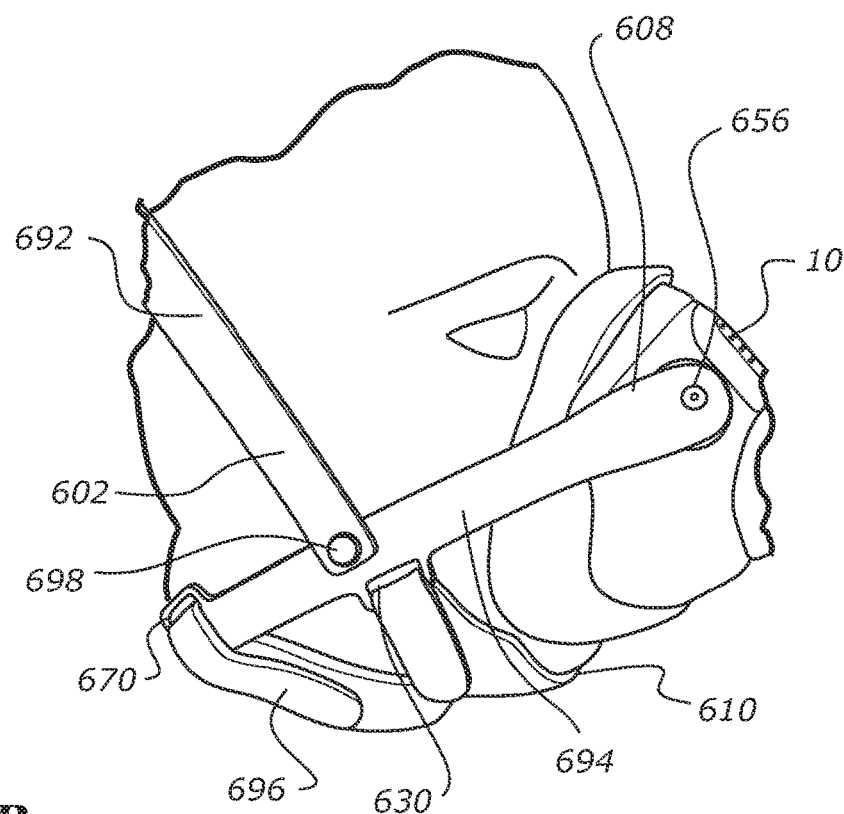
FIG. 17B illustrates a side perspective view of the headgear assembly and the interface of FIG. 17A.

FIGS. 17A-17B illustrates a headgear assembly 600 including a side arm 602 with a first or an upper member 692 and a second or a lower member 694. The headgear assembly 600 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 600 can include any features of the headgear assemblies described herein. While only one side arm 602 is shown in FIGS. 17A-17B, the other side arm 602 of the headgear assembly 600 can have the same or similar features and can be a mirror image of the illustrated side arm 602. While interface 10 is shown, any interface can be used with headgear assembly 600.

The side arm 602 includes the upper member 692. The upper member 692 of the side arm 602 includes an upper end 616. The upper end 616 is bifurcated into a top strap connection point 620 and a rear strap connection point 622. The top strap connection point 620 and the rear strap connection point 622 form an angle there between. The top strap connection point 620 is substantially vertical and the rear strap connection point 622 is substantially horizontal. The upper member 692 of the side arm 602 includes an ear arch 624. The ear arch 624 passes above the ear of the user in use. The upper member 692 of the side arm 602 includes a mid-section 626. The head gear assembly 600 includes a top strap 612 and a rear strap 614.

The side arm 602 includes the lower member 694. FIG. 17B illustrates the lower member 694. The lower member 694 is formed as an elongate extension of a connecting member 608. The lower member 694 extends towards the user's lower jaw and a location below the user's ears. The connecting member 608 is integrally formed with the lower member 694. In some embodiments, the connecting member 608 is not integrally formed with the lower member 694. In some embodiments, the connecting member 608 forms an adjustment mechanism with the side arm 602, according to any of the embodiments described herein. The connecting member 608 forms a rotational adjustment mechanism or pivot connection 656 with the interface 10.

The upper member 692 and the lower member 694 include a second rotational adjustment mechanism or pivot connection 698. The side arm 602 is formed by the upper member 692 and the lower members 694 that are pivotally coupled by the pivot connection 698. The upper member 692 and the lower members 694 are separate components. The forward lower end of the upper member 692 is pivotally coupled to a mid-point of the lower member 694. In some embodiments, the upper member 692 is pivotally coupled to the lower member 694 at a point other than a mid-point (e.g., closer to the interface 10 than the midpoint, farther from interface than the midpoint, etc.).

The lower member 694 of the side arm 602 includes a first chin strap connection point 630 and a second chin strap connection point 670. The first and second chin strap connection points 630, 670 are spaced along the length of the lower member 694. The first chin strap connection point 630 is forward of the connection with the upper member 692 and the second chin strap connection point 670 is at or near a rear or free end of the lower member 694. The first chin strap connection point 630 is closer to the interface 10 than the second chin strap connection point 670. The first chin strap connection point 630 and the second chin strap connection point 670 can form an angle there between. The angle can be approximately 180 degrees (e.g., 170 degrees, 180 degrees, 190 degrees, 200 degrees, 210 degrees, etc.). The first chin strap connection point 630 and the second chin strap connection point 670 are located on opposite sides of the lower member 690. In some embodiments, the first chin strap connection point 630 and the second chin strap connection point 670 are located on the same side of the lower member 690.

The head gear assembly 600 includes a first chin strap 610 designed to couple to the first chin strap connection point 630. The head gear assembly 600 includes a second chin strap 696 designed to couple to the second chin strap connection point 670. The lower member 694 has two chin straps 610, 696 adjustably attached to the lower member 690. The first chin strap 610 extends under the user's chin. The second chin strap 696 is spaced from the first chin strap. The second chin strap 696 extends at least partially around the user's neck.

The first chin strap 610 is near the mid-point of the lower member 694. In some embodiments, the first chin strap 610 can be attached at any location along the lower member 694. The first chin strap 610 can be attached at any location forward of the second chin strap 696. The first chin strap 610 is attached at a point forward of the pivot connection 698. The second chin strap 696 is attached at a point rearward of the pivot connection 698. The second chin strap 696 is attached at a rear end of the lower member 694.

The lower member 694 forms a lever arm where tightening the second chin strap 696 causes the lower member 694 to rotate anti-clockwise (as indicated by the arrow in FIG. 17A) and further engage the interface 10 with the user's face. In other arrangements, other mechanisms for rotating the lower member 694 relative to the upper member 692 can be employed in the place of or in addition to the second chin strap 696. For example, a length-adjustable strap or strut can be used to adjust a relative rotational position between the upper member 692 and the lower member 694.

Figure 18:
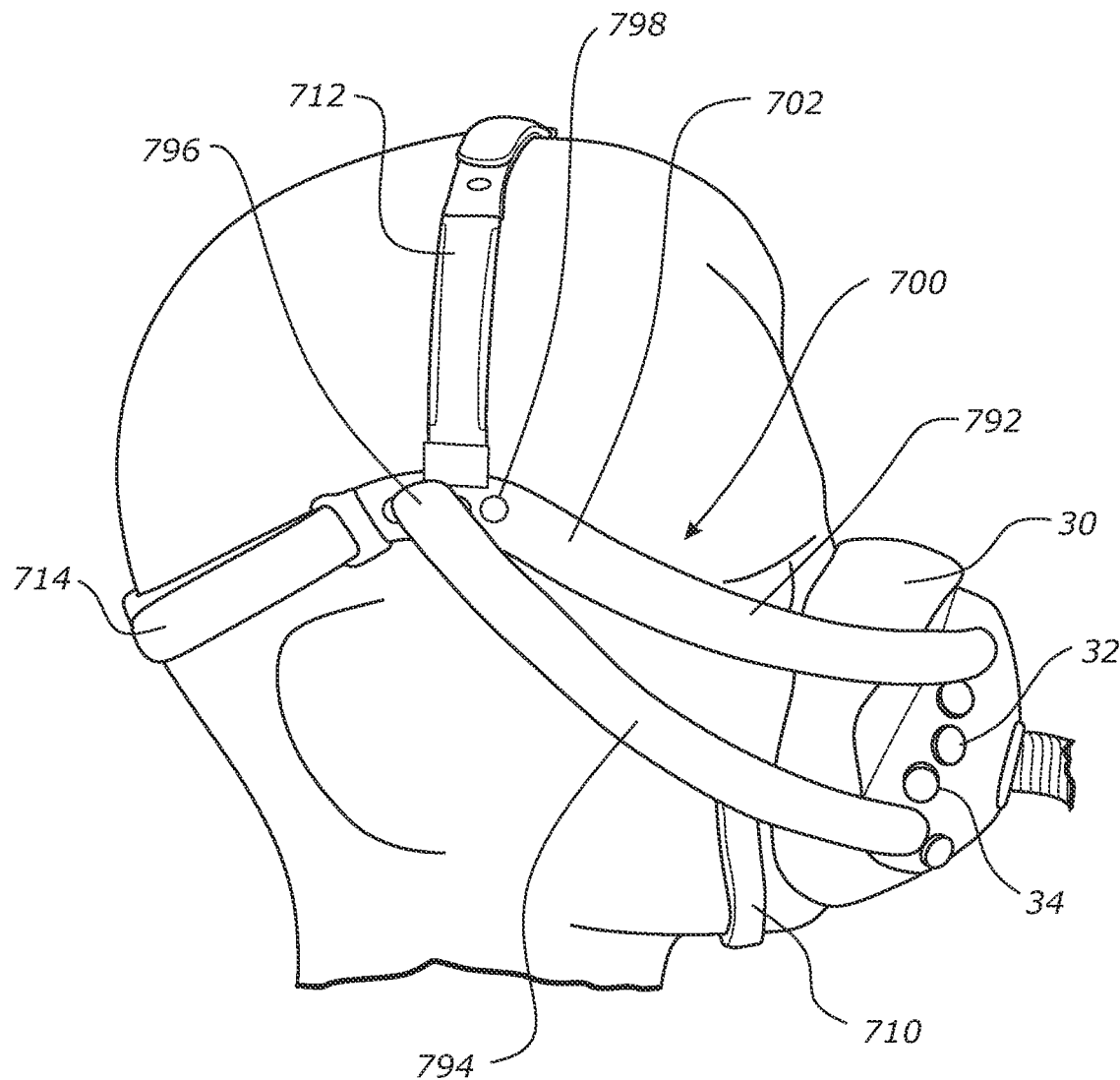
FIG. 18 illustrates a side view of a user, a headgear assembly, and an interface.

FIG. 18 illustrates an interface 30 and a headgear assembly 700 including a side arm 702 with an upper portion 792 and a lower portion 794. The headgear assembly 700 can be substantially the same as the headgear assembly 100 except as described below. Thus, any features not specifically described can be substantially the same as or similar to corresponding features of the headgear assembly 100 or other headgear assemblies described herein, or can be of another suitable arrangement. The headgear assembly 700 can include any features of the headgear assemblies described herein. While only one side arm 702 is shown in FIG. 18, the other side arm 702 can have the same or similar features and can be a mirror image of the illustrated side arm 702. The headgear assembly 700 includes the integrally formed upper portion 792 and top strap 712. The headgear assembly 700 includes the rear strap 714. The headgear assembly 700 includes the integrally formed lower portion 794 and chin strap 710.

FIG. 18 shows an interface assembly for use in respiratory therapy, the interface assembly including the interface 30 and the headgear assembly 700. Each side of the headgear assembly 700 the upper portion 792 connected to the interface 30 and adapted to extend from the interface 30 to a location above a user's ear and the lower portion 794 having a first end that connects to the upper portion 792 and a second end that connects to the interface 30 below the connection of the upper portion 792 to the interface 30. The connection location of at least one of the ends of the lower portion 794 is adjustable. The connection location of at least one of the ends of the lower portion is discretely adjustable.

FIG. 18 illustrates a plurality of connection points 32 on the interface 30. The upper portions 792 are removably connected to any one of the plurality of connection points 32 on the interface 30. The upper portions 792 include a post and aperture snap-fit connection. The upper portions 792 include the aperture and the interface 30 includes the post. In some embodiments, the upper portions 792 include the post and the interface 30 includes the apertures. Other configurations are contemplated to couple the upper portions 792 and the interface 30. In some embodiments, the upper portions 792 and the interface 30 include magnets. The upper portions 792 and the interface 30 are removably joined. In some embodiments, the upper portions 792 and the interface 30 are permanently joined. The upper portions 792 and/or the interface 30 include extra connection points 32. The extra holes and/or connection points 32 in a snap fit arrangement may be plugged with inserts 34 to maintain an air tight breathing chamber within the interface 30. The connection points 32 protrude from an outer surface of the interface 30. In some embodiments, the connection points 32 can allow the interface 30 and upper side arm 702 to pivot relative to each other. The upper portions 792 are semi-rigid.

The lower portions 794 are removably connected to any one of a plurality of connection points 32 on the interface 30. The lower portion 794 can connect via a snap fit with one or more posts and one or more holes. The lower portion 794 can connect via magnets. The lower portion 794 can connect via any other couplings or connection means. The lower portion 794 and the connection points 32 allow for incremental adjustment of the height of the lower portion 794 relative to the interface 30 and/or upper portion 792. The lower portion 794 can be incrementally and discretely adjusted. The lower portion 794 and the connection points 32 can include an adjustment arrangement including a button or post connection points 32 that is received by any one of a several spaced apart holes in the lower portion 794. The post can form a snap-fit or interference fit with the hole such that the lower portion 794 is secure. Other types of fasteners are contemplated to provide the adjustment of the lower portion 794. The lower portion 794 and the connection points 32 adjustment arrangement is considered a fit and forget configuration in which the lower portion 794 is adjusted once and there may be no need to adjust on a regular basis.

The lower portion 794 is connected to the upper portions 792 at a strap junction 796. The strap junction 796 is formed where the top strap 712 diverges from the upper portions 792. When the lower portion 794 is connected between the strap junction 796 and the interface 30, any pivoting motion of the interface 10 relative to the upper portions 792 is reduced or prevented. The lower portion 794 connects to the upper portions 792 via any one of a plurality of connection points 798 at the strap junction 796. In some methods of use, the lower portion 794 can be connected to only one connection point 798 after the lower portion 794 is connected to the interface 30 based on the fit to the user. The connection between the lower portions 794 and the strap junctions 796 allows the lower portions 794 to pivot relative to the upper portions 792. The chin strap 710 extends between the opposing lower portions 794. The plurality of connection points 32 on the interface 30 and the plurality of connection points 798 at the strap junction 796 allow the angle and distance between the upper portion 792 and lower portion 794 to be adjusted. As an example, increasing the angle between the upper portion 792 and lower portion 794 will reduce the distance between the strap junction 796 and a chin region of the interface 30 thus increasing engagement and sealing force between the chin region and a user's chin. As another example, decreasing the angle between the upper portion 792 and lower portion 794 will increase the distance between the strap junction 796 and a chin region of the interface 30 thus decreasing engagement and sealing force between the chin region and a user's chin. Adjusting the distance between the upper portion 792 and lower portion 794 can also produce differences in the engagement and the sealing force.

When fitting the interface 30, the lower portions 794 are preferably disconnected from the strap junction 796 such that the interface 30 and rest of the headgear 700 can be fitted to the user's head. The interface 30 is positioned and then the lower portions 794 along with the chin strap 710 can be pivoted/swung upwards into engagement and then connected to the strap junction 796.

Figure 19A:
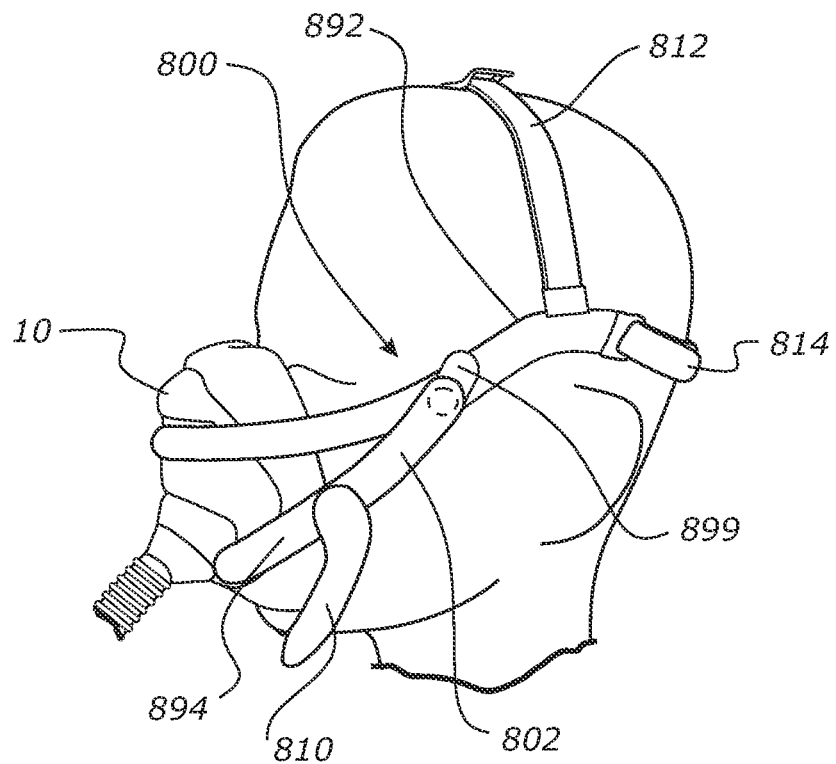
FIG. 19A illustrates a side view of a user, a headgear assembly, and an interface in a first chin strap configuration.
Figure 19B:
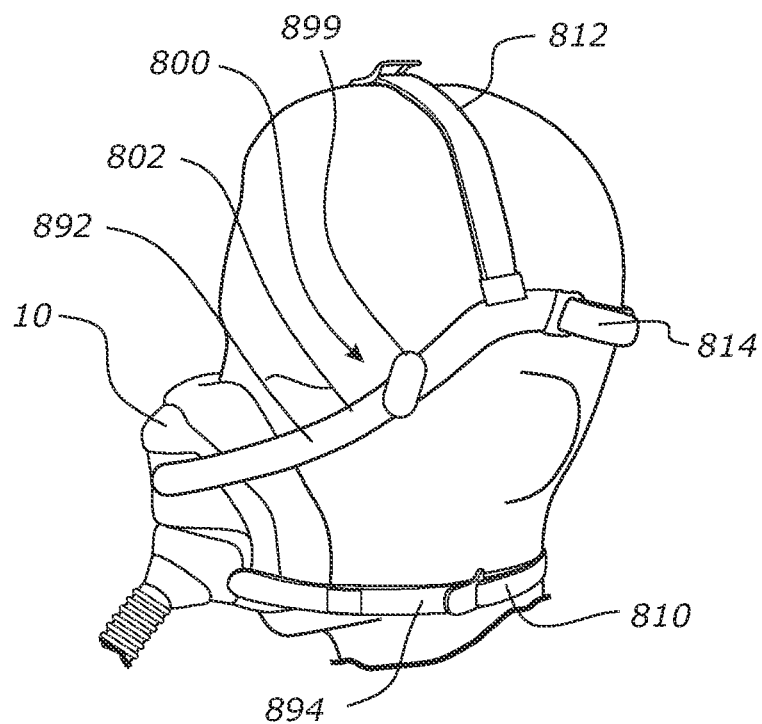
FIG. 19B illustrates a side view of the user, the headgear assembly, and the interface of FIG. 19A in a second chin strap configuration.

FIGS. 19A-19B illustrate an interface 10 and a headgear assembly 800 including a side arm 802 with an upper side arm 892 and a lower side arm 894. The headgear assembly 800 includes the integrally formed upper side arm 892 and a top strap 812. The headgear assembly 800 includes a rear strap 814. The headgear assembly 800 includes a chin strap 810. The upper and lower side arms 892, 894 are pivotally coupled to the interface 10. While only one side arm 802 is shown in FIG. 19A-19B, the other side arm 802 can have the same or similar features and can be a mirror image of the illustrated side arm 802. The headgear assembly 800 can be substantially the same as the headgear assembly 100 except as described below. The headgear assembly 800 can be substantially the same or similar to the headgear assembly 300 described herein. Thus, any features not specifically described can be substantially the same as or similar to corresponding features of the headgear assembly 100 or other headgear assemblies described herein, or can be of another suitable arrangement. The headgear assembly 800 can include any features of the headgear assemblies described herein.

The lower side arm 894 is connected to the upper side arm 892 at a strap junction 899. The strap junction 899 is at a location spaced from where the top strap 812 diverges from the upper side arm 892. The strap junction 899 is located forward of the point where the top strap 812 diverges from the upper side arm 892. When the lower side arm 894 is connected between the strap junction 899 and the interface 10, any pivoting motion of the interface 10 relative to the upper side arm 892 is reduced or prevented. The lower side arm 894 connects to the upper side arm 892 via a fastener at the strap junction 899. The fastener can be a hook and loop fastener or any other adjustment mechanism described herein. The connection between the lower side arms 894 and the strap junctions 899 allows the lower side arms 894 to pivot relative to the upper side arm 892.

The chin strap 810 is removably coupled to the lower side arm 894. FIG. 19A illustrates the chin strap 810 in a first configuration. FIG. 19A illustrates the chin strap 810 extending from a midpoint of the lower side arm 894. The chin strap 810 extends between the opposing lower side arms 894 and under the chin of the patient.

FIG. 19B illustrates the chin strap 810 in a second configuration. The chin strap 810 is connected to the rear ends of the lower side arms 894 to form a neck strap that extends around the neck of the user. The rear ends of the lower arms 894 are disconnected from a strap junction 899 and pivoted downwards towards the user's neck. The rear end of the lower side arm 894 can include a fastener that enables the lower side arm 894 to be connected to the strap junction 899 or the lateral ends of the chin strap 810.

Figure 20:
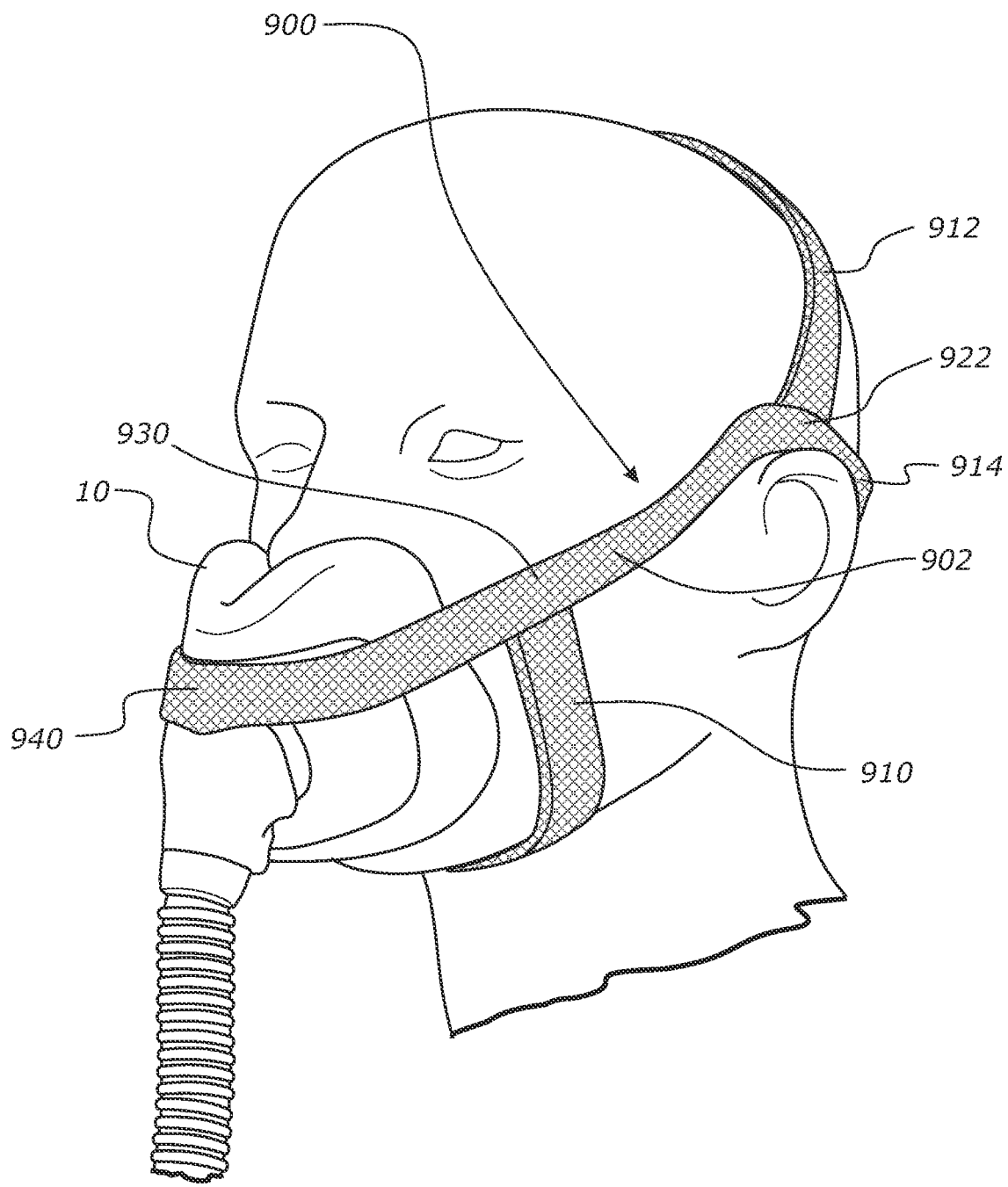
FIG. 20 illustrates a perspective view of a user, a headgear assembly, and an interface.
Figure 21:
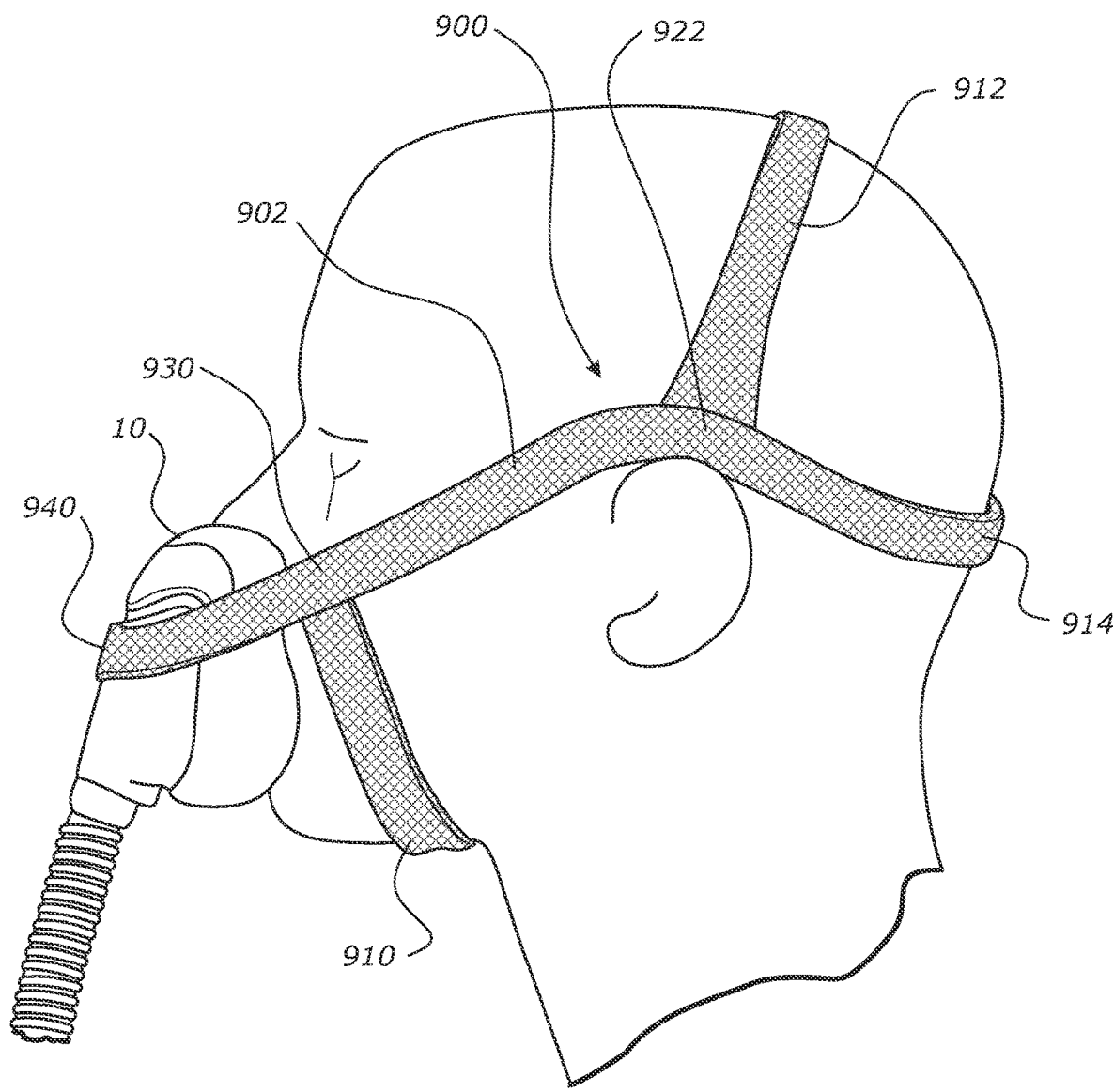
FIG. 21 illustrates a side view of the user and the headgear assembly of FIG. 20.

FIGS. 20 and 21 illustrate an interface 10 and a headgear assembly 900 including integrally formed side arms 902, chin strap 910, top strap 912, and rear strap 914. The headgear assembly 900 can be substantially the same as the headgear assembly 100,200,300, except as described below. Thus, any features not specifically described can be substantially the same as or similar to corresponding features of the headgear assembly 100,200,300 or other headgear assemblies described herein, or can be of another suitable arrangement. The headgear assembly 900 can include any features of the headgear assemblies described herein. While only one side of headgear assembly 900 is shown in FIGS. 20-21, the other side can have the same or similar features and can be the same or similar to the illustrated side depicted in FIGS. 20-21. The side arms 902 on either side of the headgear assembly 900 rest on opposite sides of the user's face, extend towards the middle of the user's face, and form a continuous loop, forming yoke portion 940 that engages interface 10 as described below. As with the headgear assembly 300 disclosed above, the side strap 902 is located above the ears and does not come into contact with the ears. As described herein, the side arms 902 are integrally formed with the chin strap 910, top strap 912, and rear strap 914. The side arm 902 includes a rear strap connection point 922 and a chin strap connection point 930, at which points the straps may be continuous with each other, formed by a single moulding process for example, or may be separate components that are permanently attached.

The headgear assembly 900 includes the integrally formed side arms 902, chin strap 910, top strap 912, and rear strap 914. The side arms 902, chin strap 910, top strap 912, and rear strap 914 are integrally formed as a single component. Any or each of the side arms 902, the chin strap 910, the top strap 912, and/or the rear strap 914 can include a textile covering. The textile covering covers at least a portion of the side arms 902, the chin strap 910, the top strap 912, and/or the rear strap 914. In some embodiments, the textile covering covers the side arms 902, the chin strap 910, the top strap 912, and/or the rear strap 914 in their entirety. The side arms 902, the chin strap 910, the top strap 912, and/or the rear strap 914 are intra-moulded. In some methods of manufacturing of the side arms 902, the chin strap 910, the top strap 912, and/or the rear strap 914, molten plastic is injected into one or more textile tubes, including one or more interconnected textile tubes, each having a lumen connected at least in part to the lumen of an adjacent tube. The plastic and the textile tubes are a unitary structure. The side arms 902 and the top strap 912 can be separately formed and later joined at connection point 922. The side arms 902 and the chin strap 910 can be separately formed and later joined at connection point 930. The side arms 902 and the rear strap 914 can be continuous, or can be separately formed and later joined at or near connection point 922. Each connection may be formed by an over-moulding process or an intra-moulding process.

The headgear assembly 900 is considered a fit and forget configuration in which the headgear assembly 900 is fitted once by selecting an appropriate size and configuration and there is no need to adjust it further. Accordingly, the side arms 902, the chin strap 910, the top strap 912, and/or the rear strap 914 are of fixed length and are not adjustable. Fitting on the user's head and donning/doffing may be possible by pivoting the chin strap forward, away from the user's neck. The headgear assembly 900 may be permanently or removably attached to interface 10, either to a mask that forms interface 10, or a mask frame that forms a component of interface 10. Removable attachment allows for easy disassembly and cleaning of the headgear assembly 900 and interface 10. Removable attachment may be achieved by various mechanisms such as snap fit or friction-fit of yoke portion 940 into or onto corresponding snap fit or friction fit features of interface 10. In alternative embodiments, any adjustment mechanism described herein, including but not limited to adjustment mechanisms 304 and/or 382, may be formed within one or more of the the chin strap 910, the top strap 912, and/or the rear strap 914.

There are several advantages associated with one or more embodiments of the headgear described herein. The headgear is used with any interface, such as a full-face mask. An advantage is that the headgear simplifies fitting. The headgear is easier to fit than traditional four point headgear. The headgear has fewer adjustments. The headgear can be positioned without undoing all of the connections. For instance, the headgear includes baseball cap style fitting, wherein the headgear is positioned in a single motion similar to putting on a baseball cap. The fit is easy, in part, because of the absence of a lower strap that passes below the user's ears.

An advantage is that the headgear of one or more embodiments described herein minimizes size and bulk compared with other commercially available headgear. The user perceives less straps and/or components on the front of the interface 10, 20, 30, which makes the interface 10, 20, 30 look less complicated and obtrusive. An advantage is that the headgear can be intuitive to use based on the connection between the headgear and the interface. In some embodiments, the headgear has a single point connection between the interface and each side of the headgear. The single point of connection can include various features and improvements. The single point of connection is a pivot connection. The single point of connection counteracts blow off forces. The single point of connection includes a component which is horizontal in use. The single point of connection is adjustable to bring the headgear toward and away from the interface. In some embodiments, the headgear has a two point connection between the interface and each side of the headgear. The two point connection can include various features and improvements. The two points of connection reduce or prevent pivoting of the headgear.

An advantage of one or more embodiments described herein is that the headgear keeps headgear straps away from the user's eyes. The headgear passes along the sides of the face of the user. The headgear passes along the user's cheeks. The headgear passes over the user's ears. The headgear passes along the crown of the head. The headgear passes along the back of the head. The headgear passes under the chin of the user. The headgear does not pass along the forehead of the user. The headgear does not pass across the eyes of the user.

An advantage of one or more embodiments described herein is that the semi-rigid side arms allow sufficient force vectors to be applied to the interface in controlled directions. The semi-rigid side arms extend along the sides of the face of the user. The semi-rigid side arms prevent or limit extension in two directions, but may allow flexing in a third direction. The third direction can allow flexing toward and away from the user's cheeks during use. The semi-rigid side arms prevent or limit extension in a horizontal and a vertical direction. The semi-rigid side arms allow sufficient force vectors to be applied to the interface to enable a good seal between the user's face and the interface. The semi-rigid side arms can provide a good seal, despite a single attachment point on each side. The semi-rigid side arms reduce or limit movement between the headgear assembly and the interface. The semi-rigid side arms are vertically rigid in use. The semi-rigid side arms are horizontally rigid in use. The rigid side arms can flex toward and away from the user's cheeks in use.

An advantage of one or more embodiments described herein is that the headgear assembly retains its shape when not in use. The headgear assembly is held in an open configuration, by the semi-rigid side arms, when the headgear assembly is not in use. The open configuration improves the ease with which the headgear assembly and interface can be fitted to a user. The open configuration can also improve usability as the straps do not tangle as easily. In the open configuration, the user can visualize how to position and use the headgear assembly.

An advantage of one or more embodiments described herein is that the headgear assembly includes semi-rigid side arms which eliminate the need for a forehead support. The side arms include a semi-rigid plastic material. In some embodiments, the side arms include any semi-rigid material. The headgear assembly provides a clear line of sight which makes the headgear assembly feel less intrusive to the user. The headgear assembly also allows the user to wear glasses while wearing the headgear assembly due to the elimination of the forehead support. The semi-rigid arms are placed to counteract forces. In use, the semi-rigid side arms are placed above the ears of the user. In use, the semi-rigid side arms are placed down the cheeks of the user. The semi-rigid side arms are held in position with the top strap and the rear strap. The top strap and the rear strap include a wider section. The semi-rigid side arms are held in position by the chin strap. The chin strap allows for the elimination of the forehead support.

An advantage of one or more embodiments described herein is that the headgear assembly includes an adjustable or pivotable connection to the interface. The headgear assembly includes a connecting member. The connecting member includes a pivot connection. In some embodiments, the connecting member does not include a pivot connection. An advantage of one or more embodiments described herein is that the headgear assembly includes a connection to the interface to counteract forces. The connecting member is substantially horizontal in use. The connecting member is substantially horizontal to counteract blow off forces. The blow off forces are forces that act to separate the interface from the user. The interface in connected to an air inlet. The air delivered to the air inlet, and subsequently to the user, exerts a pressure on the face of the user. This pressure can be directed from the air inlet toward the user in a horizontal direction. The interface tends to move away from the user in a horizontal direction, if the blow off forces are not counteracted. The horizontal portion of the connecting member and/or the horizontal portion of the side arm can reduce or prevent the separation between the interface and the user.

An advantage of one or more embodiments described herein is that the headgear assembly includes a chin strap. The blow off forces can function as forces that cause the chin strap to ride up. The chin strap, in combination with the horizontal portion of the connecting member and/or side arm, can reduce or prevent the separation between the interface and the user. The chin strap prevents movement of the headgear assembly. In some embodiments, the chin strap is the only strap that is disconnected or adjusted to remove the headgear assembly. In some embodiments, the chin strap is the only strap that is connected by the user in use. The rear strap and the top strap have a set-and-forget configuration. The rear strap and the top strap stay connected when the user removes the headgear assembly. In some embodiments, the chin strap is convertible to a neck strap. The chin strap can help prevent the user's jaw from dropping and causing leaks.

An advantage of one or more embodiments described herein is that the headgear includes an adjustment mechanism. The adjustment mechanism provides a linear adjustment between the semi-rigid side arms and the interface. The adjustment mechanism provides forward and backward adjustment such as through an adjustment mechanism or biasing elastic. The adjustment mechanism adjusts to fit a variety of faces. The adjustment mechanism provides a telescoping arrangement. The adjustment mechanism extends the rigid connection to the interface. The adjustment mechanism extends from the side arm in a substantially horizontal direction. Soft straps can allow the interface to move, but the semi-rigid side arms and additional rigid components such as the connecting member can reduce or prevent this movement. The adjustment mechanism can be considered a translation mechanism. The adjustment mechanism can allow the headgear assembly to translate relative to the interface. The adjustment mechanism includes a ratchet. The adjustment mechanism includes two interlocking rails. The adjustment mechanism includes two telescoping members. The adjustment mechanism includes a biasing member to bias the interface and the headgear assembly toward each other.

An advantage of one or more embodiments described herein is that the headgear assembly includes headgear adjustment technology. The adjustment mechanism is self-fit in which the adjustment mechanism moves the interface and the headgear assembly toward each other. The headgear adjustment technology includes a first elongate member and a second elongate member slidably engaged with the first elongate member. The first elongate member and the second elongate member are configured to enable adjustment of the length of the adjustment mechanism by changing an amount of overlap between the first and second elongate members. The headgear adjustment technology includes a restriction mechanism or biasing member configured to provide resistance against decreasing the amount of overlap between the first and second elongate members. The headgear adjustment technology includes a retraction means configured to apply a retraction force to the first elongate member that increases the amount of overlap between the first and second elongate members. The adjustment mechanism includes a direction lock. The adjustment mechanism allows for retraction. The adjustment mechanism includes a biasing elastic to automatically fit the user. The adjustment mechanism can overcome a locking force manually. The adjustment mechanism is calibrated to resist blow off.

An advantage of one or more embodiments described herein is that the headgear assembly includes a pivot mechanism. The pivot mechanism is located at the connection between the connecting member and the interface. The pivot mechanism allows deliberate angular adjustment of the interface. The pivot mechanism maintains the angular adjustment between the interface and the headgear assembly. The pivot mechanism maintains the relative position between the interface and the headgear assembly through friction. The pivot is located about a midpoint of the interface. The pivot is at a center of rotation of the interface. The pivot is positioned to reduce inadvertent torqueing or movement of the interface. The pivot is positioned such that the interface can move toward the nose or the chin.

An advantage of one or more embodiments described herein is that the headgear assembly includes a pivot that is vertically higher than the adjustment mechanism. The headgear assembly includes two segments that form an upward extension of semi-rigid side arm. The two segments position the semi-rigid side arm below the pivot. The two segments position the adjustment mechanism below the pivot. The two segments position the male component of the adjustment mechanism below the pivot. The two segments position the adjustment mechanism horizontally. The two segments position the extension of the side arm horizontally. This position can balance the forces exerted on the interface. This position can enable the pivot to be centrally located. This position can enable the pivot to be located at a center of rotation of the interface. This position can reduce torque of the interface due to blow off forces. The pivot axes are centrally located on the lateral sides of the interface. In some embodiments, the pivot axes are located above the air inlet.

An advantage of one or more embodiments described herein is that the headgear includes a portion of the semi-rigid side arm positioned below the air inlet. The pivot mechanism is positioned near the air inlet. The connecting member includes two segments which enable the connecting member to be positioned at least partially below the air inlet. The semi-rigid side arm includes two segments which enable the semi-rigid side arm to be positioned below the air inlet. The two segments can include an elbow or bend with a first segment extending downward and/or backward and a second segment extending horizontally. The forces from the air inlet are horizontal and the counteracting forces from the semi-rigid side arm are horizontal. A lower portion of the semi-rigid side arm is below the midpoint or geometric center of the interface. The semi-rigid side arm is below the geometric center of the interface. The portion of the semi-rigid side arm is positioned low on the user's face.

An advantage of one or more embodiments described herein is that the headgear assembly includes a transition relative to the pivot axis. The pivot axes are centrally located on the lateral sides of the interface. The pivot axes are skewed relative to a vertical plane. The pivot axes are skewed relative to a horizontal plane. The lateral sides of the interface can be angled to form a triangle. The pivot axes are perpendicular to the lateral sides. The transition is a rigid twist in the connecting member. The transition positions the adjustment mechanism to be horizontal in use. The transition positions the adjustment mechanism to lie in a vertical plane. The transition positions the pull tab loop to lie in a vertical plane. The transition can enable free, horizontal movement of the components of the adjustment mechanism. The transition provides an offset from the interface. The transition allows for a flush pivot connection with the interface while orienting other components such as the adjustment mechanism in a desired orientation.

An advantage of one or more embodiments described herein is that the headgear assembly includes one or more intra-moulded features. The semi-rigid side arms are intra-moulded. A textile material is formed into a tube and a molten plastic is injected in between the tube. The intra-moulded side arm includes a cover textile surrounding a plastic core. The intra-moulded feature can be an integrated plastic with textile covering. The cover layer can be constructed from a soft fabric, textile, foam or similar cushioning materials. The core may be formed by inserting a semi-rigid plastic into the cavity of the cover layer. The side arms and the top strap are intra-moulded. The side arms and the rear strap are intra-moulded. The intra-moulded component allows for adjustment. The intra-moulded component allows for discrete adjustment through one or more connection points or strap junctions. The intra-moulded component includes one or more guide loops. The guide loop restricts the pivot motion or rotation of the semi-rigid side arm. The guide loop maintains the rigidity of the side arm.

Any of the features of headgear assemblies described herein can be combined. Additional or alternative features include the following. In some embodiments, the headgear assembly is for a full-face or nasal interface. In some embodiments, the headgear includes a pair of opposing, semi-rigid side arms that extend between an interface and a location above the user's ears, across the user's cheeks. In some embodiments, each of the side arms is coupled to the interface at a single location. In some embodiments, the side arms are pivotally coupled to the interface. In some embodiments, a top strap is provided that extend between the side arms, over the top of a user's head. In some embodiments, a rear strap is provided that extends between the side arms, around the rear of the user's head. In some embodiments, a chin strap is provided that extends between the pair of side arms below the user's chin. In some embodiments, the headgear assembly includes an adjustment mechanism that allows the interface to move relative to the side arms. In some embodiments, the adjustment mechanism essentially allows adjustment of the length of the side arms. In some embodiments, the adjustment mechanism includes a pair of members or components that are telescopically engaged.

In some embodiments, the headgear assembly allows for rotation of the side arms. In some embodiments, the headgear assembly allows for translation of the side arms. In some embodiments, the headgear includes a pair of side arms. In some embodiments, each side arm includes a translational adjustment mechanism configured to allow translational adjustment of the side arm. In some embodiments, each side arm includes a rotating adjustment mechanism configured to allow rotational adjustment of the side arm. In some embodiments, the translational adjustment mechanism includes a pair of members or components that are telescopically engaged. In some embodiments, rotating adjustment mechanism includes a pivot connection.

In some embodiments, the headgear assembly includes two rotation or pivot points. In some embodiments, the headgear assembly includes two chin straps. In some embodiments, the headgear assembly is for a patient interface. In some embodiments, the headgear assembly includes a pair of side arms. In some embodiments, each side arm includes a first rotational adjustment mechanism configured to allow rotational adjustment of the side arm. In some embodiments, each side arm includes a second rotational adjustment mechanism configured to allow rotational adjustment of the side arm. In some embodiments, the first and second rotational adjustment mechanisms spaced apart along the side arm. In some embodiments, the headgear assembly includes a top strap, a rear strap and first and second chin straps. In some embodiments, the chin straps are spaced apart from each other. In some embodiments, the chin straps extend between the pair of side arms.

In some embodiments, the headgear assembly includes a transition. In some embodiments, the transition is between a pivot connection and a male component of a connection member. The transition twists to change the plane that the male component lies in. The upper edge is twisted outwards relative to the lower edge, so that the male component lies along a substantially vertical plane. In some embodiments, the headgear includes an upward extension of the side arm towards pivot point.

In some embodiments, the headgear includes two side arms. In some embodiments, each side of the headgear has a first side strap extending from an interface to a location above the user's ear. In some embodiments, each side of the headgear has a second side strap having a first end that connects to the first side strap and a second end that connects to the interface below the connection of the first side strap. In some embodiments, the connection locations of the ends of the second strap are discretely adjustable. In some embodiments, the headgear includes a strap that is reconfigurable between a chin strap and a rear neck strap.

What is claimed is:

1. A headgear assembly comprising:
    a pair of side arms, and
    a pair of connecting members, each connecting member configured to be coupled to an interface by a pivot connection;
    wherein one of the pair of side arms is configured to be coupled to one of the pair of connecting members by a translational adjustment mechanism, wherein the translational adjustment mechanism comprises a male component configured to be inserted into a female component in a telescoping manner,
    wherein each one of the connecting members is located in between a respective one of the pair of side arms and the pivot connection; and
    wherein each side arm comprises a pull tab, wherein the pull tab comprises a fastener near a free end of the pull tab and a fixed end coupled to a rear end of the female component.

2. The headgear assembly of claim 1, wherein each connecting member is integrally formed with the male component.

3. The headgear assembly of claim 1, wherein each side arm comprises a support, wherein the support couples to the female component.

4. The headgear assembly of claim 1, wherein each side arm is integrally formed with the female component.

5. The headgear assembly of claim 1, wherein the free end of the pull tab is configured to pass through a pull tab loop.

6. The headgear assembly of claim 5, wherein the connecting member comprises the pull tab loop.

7. The headgear assembly of claim 1, wherein the pull tab limits or prevents further extension movement of the translational adjustment mechanism once the fastener is secured.

8. The headgear assembly of claim 1, wherein the male component and the female component comprise different materials.

9. The headgear assembly of claim 1, wherein the male component and the female component of the translational adjustment mechanism are substantially rigid and straight in order to enable linear sliding and minimize binding during translational adjustment.

10. The headgear assembly of claim 1, wherein the male component and the female component are horizontal in use.

11. The headgear assembly of claim 1, wherein the male component and the female component are configured to provide adjustment in a direction of blow-off forces.

12. The headgear assembly of claim 1, wherein each pivot connection comprises a pivot axis.

13. The headgear assembly of claim 12, wherein each pivot axis is located above an air inlet.

14. The headgear assembly of claim 1, wherein each pivot connection has discrete positions.

15. A headgear assembly comprising:
    a pair of side aims, and
    a pair of connecting members, each connecting member configured to be coupled to an interface and receive a portion of one of the pair of side arms;
    wherein one of the pair of side arms is configured to be coupled to one of the pair of connecting members by a translational adjustment mechanism, wherein the translational adjustment mechanism comprises a male component and a female component, wherein the female component comprises a housing configured to receive the male component in a sliding or telescopic manner; and
    wherein each side arm comprises a pull tab, wherein the pull tab comprises a fastener near a free end of the pull tab and a fixed end coupled to a rear end of the female component.

16. The headgear assembly of claim 15, wherein each connecting member is configured to be coupled to the interface by a rotating adjustment mechanism.

17. The headgear assembly of claim 15, wherein a pull tab limits or prevents further extension movement of the translational adjustment mechanism once a fastener of the pull tab is secured.

18. A headgear assembly comprising:
    a first side arm and a second side arm, and
    a first connecting member configured to be coupled to an interface and a second connecting member configured to be coupled to the interface, the first connecting member configured to receive a portion of the first side arm and the second connecting member configured to receive a portion of the second side arm;
    wherein the first side arm is configured to be coupled to the first connecting member by a first translational adjustment mechanism, wherein the first translational adjustment mechanism comprises a first male component configured to be inserted into a first female component in a telescoping manner,
    wherein the first side arm comprises a pull tab, wherein the pull tab comprises a fastener near a free end of the pull tab and a fixed end coupled to a rear end of the first female component,
    wherein the second side arm is configured to be coupled to the second connecting member by a second translational adjustment mechanism, wherein the second translational adjustment mechanism comprises a second male component configured to be inserted into a second female component in a telescoping manner; and
    wherein the second side arm comprises a pull tab, wherein the pull tab comprises a fastener near a free end of the pull tab and a fixed end coupled to a rear end of the second female component.

* * * * *